(12) United States Patent
Borody

(10) Patent No.: US 11,040,073 B2
(45) Date of Patent: Jun. 22, 2021

(54) COMPOSITIONS AND METHODS FOR TREATING DIVERTICULITIS AND RELATED DISORDERS

(71) Applicant: Crestovo Holdings LLC, Somerville, MA (US)

(72) Inventor: Thomas Julius Borody, Five Dock (AU)

(73) Assignee: Finch Therapeutics Holdings LLC, Someville, MA (US)

( * ) Notice: Subject to any disclaimer, the term of this patent is extended or adjusted under 35 U.S.C. 154(b) by 42 days.

(21) Appl. No.: 16/603,170

(22) PCT Filed: Apr. 4, 2018

(86) PCT No.: PCT/US2018/026074
§ 371 (c)(1),
(2) Date: Oct. 4, 2019

(87) PCT Pub. No.: WO2018/187464
PCT Pub. Date: Oct. 11, 2018

(65) Prior Publication Data
US 2020/0038455 A1 Feb. 6, 2020

Related U.S. Application Data

(60) Provisional application No. 62/482,159, filed on Apr. 5, 2017.

(51) Int. Cl.
| | | |
|---|---|---|
| *A61K 36/00* | (2006.01) | |
| *A61K 35/38* | (2015.01) | |
| *A61K 9/19* | (2006.01) | |
| *A61K 9/48* | (2006.01) | |
| *A61K 35/74* | (2015.01) | |
| *A61K 45/06* | (2006.01) | |
| *A61P 1/00* | (2006.01) | |

(52) U.S. Cl.
CPC ............... *A61K 35/38* (2013.01); *A61K 9/19* (2013.01); *A61K 9/48* (2013.01); *A61K 35/74* (2013.01); *A61K 45/06* (2013.01); *A61P 1/00* (2018.01)

(58) Field of Classification Search
None
See application file for complete search history.

(56) References Cited

U.S. PATENT DOCUMENTS

| | | |
|---|---|---|
| 3,192,116 A | 6/1965 | Mose et al. |
| 3,320,130 A | 5/1967 | Henry |
| 3,713,836 A | 1/1973 | Carlsson |
| 4,098,728 A | 7/1978 | Rosenblatt |
| 4,309,782 A | 1/1982 | Paulin |
| 4,332,790 A | 6/1982 | Sozzi et al. |
| 4,335,107 A | 6/1982 | Snoeyenbos et al. |
| 4,394,377 A | 7/1983 | Spires |
| 4,452,779 A | 6/1984 | Cockerill |
| 4,536,409 A | 8/1985 | Farrell et al. |
| 4,657,762 A | 4/1987 | Mikkola et al. |
| 4,710,379 A | 12/1987 | Kawai et al. |
| 4,892,731 A | 1/1990 | Arai et al. |
| 4,975,286 A | 12/1990 | Hechter |
| 5,213,807 A | 5/1993 | Chemburkar et al. |
| 5,266,315 A | 11/1993 | Taguchi et al. |
| 5,443,826 A | 8/1995 | Borody |
| 5,728,380 A | 3/1998 | Allen et al. |
| 5,800,821 A | 9/1998 | Acheson et al. |
| 5,837,238 A | 11/1998 | Casas et al. |
| 5,858,356 A | 1/1999 | Wolf et al. |
| 5,902,578 A | 5/1999 | Halpin-Dohnalek et al. |
| 5,902,743 A | 5/1999 | Luchansky et al. |
| 6,087,386 A | 7/2000 | Chen et al. |
| 6,162,464 A | 12/2000 | Jacob et al. |
| 6,245,740 B1 | 6/2001 | Goldenberg et al. |
| 6,284,274 B1 | 9/2001 | Merrill et al. |
| 6,428,783 B1 | 8/2002 | Khachatrian et al. |
| 6,479,051 B1 | 11/2002 | Bruce |
| 6,514,531 B1 | 2/2003 | Alaux et al. |
| 6,645,530 B1 | 11/2003 | Borody |
| 6,649,397 B1 | 11/2003 | Nakamura |
| 6,756,032 B1 | 6/2004 | Tepper et al. |
| 6,926,907 B2 | 8/2005 | Plachetka |
| 6,979,674 B1 | 12/2005 | Goldenberg et al. |

(Continued)

FOREIGN PATENT DOCUMENTS

| | | |
|---|---|---|
| AU | 2001276160 B2 | 6/2007 |
| CA | 1333564 | 12/1994 |

(Continued)

OTHER PUBLICATIONS

Mandalia, Diverticulitis after fecal microbiota transplant for C. difficile infection. The American journal of gastroenterology, (Dec. 2014) vol. 109, No. 12, pp. 1956-1957 (Year: 2014).*
"Autoimmune Disease List," *American Autoimmune Related Diseases Association*, pp. 1-4 (2017) <https://www.aarda.org/diseaselist/>.
"Certain infectious and parasitic diseases (A00-B99)," *International Statistical Classification of Diseases and Related Health Problems*, 10th Revision (ICD-10)—WHO Version, Chapter 1, pp. 1 (2016) <www.apps.who.int/classifications/icd1 0/browse/2016/en#II>.
"Spore-Forming Gram-Positive Bacilli: *Bacillus* and *Clostridium* Species," *Jawetz, Melnick, & Adelberg's Medical Microbiology*, 26th Edition, Chapter 11, pp. 1-15 (2012).

(Continued)

*Primary Examiner* — Qiuwen Mi
(74) *Attorney, Agent, or Firm* — Arnold & Porter Kaye Scholer LLP; David Marsh; Scott Douglas

(57) ABSTRACT

The present disclosure is in the field of pharmaceutical compositions suitable for the treatment of diseases in mammals. The disclosure provides novel compositions comprising non-pathogenic fecal microbes for treating recurrent diverticulitis and related diseases. The disclosure also provides methods for treating a subject with the compositions disclosed herein.

20 Claims, No Drawings

(56) References Cited

U.S. PATENT DOCUMENTS

| | | |
|---|---|---|
| 6,984,513 B2 | 1/2006 | Brown et al. |
| 7,018,629 B2 | 3/2006 | Jacob et al. |
| 7,374,753 B1 | 5/2008 | Farmer et al. |
| 7,541,091 B2 | 6/2009 | Sisson et al. |
| 7,749,509 B2 | 7/2010 | Cobb et al. |
| 7,763,276 B1 | 7/2010 | Shodai et al. |
| 7,799,341 B2 | 9/2010 | Porzio et al. |
| 7,815,956 B2 | 10/2010 | Lee et al. |
| 7,846,475 B2 | 12/2010 | Shiraishi et al. |
| 7,888,062 B1 | 2/2011 | Garner et al. |
| 7,998,510 B2 | 8/2011 | Caswell |
| 8,168,171 B2 | 5/2012 | Mogna et al. |
| 8,460,648 B2 | 6/2013 | Borody |
| 8,586,029 B2 | 11/2013 | Kasper et al. |
| 8,637,297 B2 | 1/2014 | Fernandez et al. |
| 8,658,153 B2 | 2/2014 | Daube et al. |
| 8,771,673 B2 | 7/2014 | Cobb et al. |
| 9,040,036 B2 | 5/2015 | Borody |
| 9,050,358 B2 | 6/2015 | Borody |
| 9,308,226 B2 | 4/2016 | Borody |
| 9,320,763 B2 | 4/2016 | Borody |
| 9,408,872 B2 | 8/2016 | Borody |
| 9,468,658 B2 | 10/2016 | Borody |
| 9,572,841 B2 | 2/2017 | Borody |
| 9,572,842 B2 | 2/2017 | Borody |
| 9,610,308 B2 | 4/2017 | Borody |
| 9,623,056 B2 | 4/2017 | Borody |
| 9,719,144 B2 | 8/2017 | Krajmalnik-Brown et al. |
| 2001/0014322 A1 | 8/2001 | Chen et al. |
| 2002/0013270 A1 | 1/2002 | Bolte |
| 2002/0022019 A1 | 2/2002 | Laulund |
| 2002/0039599 A1 | 4/2002 | Lin et al. |
| 2003/0092163 A1 | 5/2003 | Collins et al. |
| 2003/0092724 A1 | 5/2003 | Kao et al. |
| 2003/0147858 A1 | 8/2003 | Renaud et al. |
| 2004/0062757 A1 | 4/2004 | Finegold |
| 2004/0167062 A1 | 8/2004 | Bolte |
| 2004/0170617 A1 | 9/2004 | Finegold |
| 2004/0223956 A1 | 11/2004 | Naidu et al. |
| 2006/0076536 A1 | 4/2006 | Barshied |
| 2006/0099197 A1 | 5/2006 | Farmer |
| 2006/0115465 A1 | 6/2006 | Macfarlane et al. |
| 2006/0177424 A1 | 8/2006 | Cobb et al. |
| 2006/0275223 A1 | 12/2006 | Burr |
| 2007/0059296 A1 | 3/2007 | Chen |
| 2008/0254009 A1 | 10/2008 | Finegold |
| 2008/0299197 A1 | 12/2008 | Toneguzzo et al. |
| 2010/0112003 A1 | 5/2010 | Collins et al. |
| 2010/0178349 A1 | 7/2010 | Kolter et al. |
| 2010/0178413 A1 | 7/2010 | Gorris |
| 2010/0184785 A1 | 7/2010 | Kolter et al. |
| 2010/0222311 A1 | 9/2010 | Thommes et al. |
| 2010/0226866 A1 | 9/2010 | Yamashiro et al. |
| 2010/0233278 A1 | 9/2010 | Ookaa et al. |
| 2010/0239667 A1 | 9/2010 | Hemmingsen et al. |
| 2010/0247489 A1 | 9/2010 | Saur-Brosch et al. |
| 2010/0247665 A1 | 9/2010 | Takahashi |
| 2010/0255231 A1 | 10/2010 | Chau et al. |
| 2010/0255307 A1 | 10/2010 | Gonze et al. |
| 2010/0278930 A1 | 11/2010 | Okumura et al. |
| 2010/0285164 A1 | 11/2010 | Schaible et al. |
| 2010/0289164 A1 | 11/2010 | Porzio et al. |
| 2010/0297031 A1 | 11/2010 | Ubeda Perez et al. |
| 2011/0008554 A1 | 1/2011 | Chen et al. |
| 2011/0045222 A1 | 2/2011 | Peters |
| 2011/0081320 A1 | 4/2011 | Westall et al. |
| 2011/0200570 A1 | 8/2011 | Mosbaugh et al. |
| 2011/0218216 A1 | 9/2011 | Vivek et al. |
| 2012/0020941 A1 | 1/2012 | Wacklin et al. |
| 2012/0039853 A1 | 2/2012 | Corveleyn et al. |
| 2012/0064133 A1 | 3/2012 | Chauhan et al. |
| 2012/0087895 A1 | 4/2012 | Mazmanian et al. |
| 2012/0183612 A1 | 7/2012 | Brogmann et al. |
| 2012/0252775 A1 | 10/2012 | Finegold |
| 2013/0045274 A1 | 2/2013 | Hlavka |
| 2013/0195804 A1 | 8/2013 | Borody |
| 2013/0259899 A1 | 10/2013 | Allen-Vercoe et al. |
| 2013/0316394 A1 | 11/2013 | Stimpson |
| 2014/0065132 A1 | 3/2014 | Hsiao et al. |
| 2014/0086877 A1 | 3/2014 | Hlavka |
| 2014/0147417 A1 | 5/2014 | Sadowsky et al. |
| 2014/0147425 A1 | 5/2014 | Henn et al. |
| 2014/0234260 A1 | 8/2014 | Borody |
| 2014/0255351 A1 | 9/2014 | Berstad et al. |
| 2014/0328803 A1 | 11/2014 | McKenzie et al. |
| 2014/0341921 A1 | 11/2014 | Honda et al. |
| 2014/0342438 A1 | 11/2014 | Allen-Vercoe et al. |
| 2014/0363397 A1 | 12/2014 | Allen-Vercoe et al. |
| 2014/0363398 A1 | 12/2014 | Jones et al. |
| 2015/0044173 A1 | 2/2015 | Jones et al. |
| 2015/0050246 A1 | 2/2015 | Jones et al. |
| 2015/0093360 A1 | 4/2015 | McKenzie et al. |
| 2015/0143557 A1 | 5/2015 | Honda et al. |
| 2015/0152484 A1 | 6/2015 | Krajmalnik-Brown et al. |
| 2015/0190435 A1 | 7/2015 | Henn et al. |
| 2015/0224152 A1 | 8/2015 | Littman et al. |
| 2015/0238544 A1 | 8/2015 | Jones et al. |
| 2015/0238545 A1 | 8/2015 | Borody |
| 2015/0238546 A1 | 8/2015 | Borody |
| 2015/0297642 A1 | 10/2015 | Borody |
| 2015/0306144 A1 | 10/2015 | Borody |
| 2015/0306155 A1 | 10/2015 | Borody |
| 2015/0306156 A1 | 10/2015 | Borody |
| 2015/0374761 A1 | 12/2015 | Sadowsky et al. |
| 2016/0089363 A1 | 3/2016 | Borody |
| 2016/0151429 A1 | 6/2016 | Borody |
| 2016/0151431 A1 | 6/2016 | Borody |
| 2016/0151432 A1 | 6/2016 | Borody |
| 2016/0151433 A1 | 6/2016 | Borody |
| 2016/0158294 A1 | 6/2016 | Von Maltzahn et al. |
| 2016/0279178 A1 | 9/2016 | Borody |
| 2016/0279179 A1 | 9/2016 | Borody |
| 2016/0331791 A1 | 11/2016 | Borody |
| 2016/0339065 A1 | 11/2016 | Adams et al. |
| 2017/0216378 A1 | 8/2017 | Honda et al. |
| 2017/0246220 A1 | 8/2017 | Sato et al. |
| 2017/0348360 A1 | 12/2017 | Borody |
| 2018/0153943 A1 | 6/2018 | Borody |
| 2018/0256652 A1 | 9/2018 | Borody |
| 2019/0015460 A1 | 1/2019 | Borody |
| 2019/0015461 A1 | 1/2019 | Borody |
| 2019/0015462 A1 | 1/2019 | Borody |
| 2019/0046589 A1 | 2/2019 | Borody |

FOREIGN PATENT DOCUMENTS

| | | |
|---|---|---|
| CA | 2 391 422 A1 | 1/2004 |
| CN | 1561387 A | 1/2005 |
| CN | 101496819 A | 8/2009 |
| CN | 201441672 U | 4/2010 |
| DE | 2 134 179 A1 | 1/1973 |
| EP | 303 426 A2 | 2/1989 |
| EP | 456 418 A2 | 11/1991 |
| EP | 433 299 B1 | 5/1998 |
| EP | 1 514 572 A2 | 3/2005 |
| EP | 1 514 572 A3 | 11/2006 |
| EP | 1 800 688 A1 | 6/2007 |
| EP | 1 514 572 B1 | 12/2008 |
| EP | 2 823 822 B1 | 10/2016 |
| FR | 1275 M | 5/1962 |
| FR | 2427 M | 3/1964 |
| FR | 2828 M | 10/1964 |
| FR | 5528 M | 11/1967 |
| FR | 2 244 464 A1 | 4/1975 |
| GB | 1271674 A | 4/1972 |
| JP | 64-67192 | 3/1989 |
| JP | H05-306221 A | 11/1993 |
| JP | H07-242539 A | 9/1995 |
| JP | H07-242557 A | 9/1995 |
| JP | 3 144 556 B2 | 3/2001 |
| JP | 2004-501095 | 1/2004 |
| JP | 2005-118544 A | 5/2005 |
| JP | 2008-106066 | 5/2008 |
| JP | 2010-513359 | 4/2010 |

(56) References Cited

FOREIGN PATENT DOCUMENTS

| | | |
|---|---|---|
| JP | 2010-520234 A | 6/2010 |
| KR | 10-0913405 B1 | 8/2009 |
| WO | WO 90/01335 A1 | 2/1990 |
| WO | WO 95/33046 A1 | 12/1995 |
| WO | WO 96/11014 A1 | 4/1996 |
| WO | WO 98/13068 A1 | 4/1998 |
| WO | WO 00/07571 A2 | 2/2000 |
| WO | WO 00/015760 | 3/2000 |
| WO | WO 00/42168 A2 | 7/2000 |
| WO | WO 02/07741 A1 | 1/2002 |
| WO | WO 03/033681 A2 | 4/2003 |
| WO | WO 2005/017095 A2 | 2/2005 |
| WO | WO 2006/127355 A2 | 11/2006 |
| WO | WO 2008/077614 A2 | 7/2008 |
| WO | WO 2008/105715 A2 | 9/2008 |
| WO | WO 2008/117266 A2 | 10/2008 |
| WO | WO 2008/117267 A2 | 10/2008 |
| WO | WO 2008/077614 A3 | 1/2009 |
| WO | WO 2009/024429 A2 | 2/2009 |
| WO | WO 2009/026306 A2 | 2/2009 |
| WO | WO 2009/055362 A1 | 4/2009 |
| WO | WO 2010/040020 A1 | 4/2010 |
| WO | WO 2011/033310 A1 | 3/2011 |
| WO | WO 2011/094027 A1 | 8/2011 |
| WO | WO 2011/110347 A2 | 9/2011 |
| WO | WO 2011/151941 A1 | 12/2011 |
| WO | WO 2012/013861 A2 | 2/2012 |
| WO | WO 2012/016287 A2 | 2/2012 |
| WO | WO 2012/045150 A1 | 4/2012 |
| WO | WO 2012/122478 A1 | 9/2012 |
| WO | WO 2012/016287 A3 | 11/2012 |
| WO | WO 2013/037067 A1 | 3/2013 |
| WO | WO 2013/090825 A1 | 6/2013 |
| WO | WO 2014/070014 A1 | 5/2014 |
| WO | WO 2014/078911 A1 | 5/2014 |
| WO | WO 2014/152338 A1 | 9/2014 |
| WO | WO 2014/152484 A1 | 9/2014 |
| WO | WO 2015/006355 A2 | 1/2015 |
| WO | WO 2015/051323 A1 | 4/2015 |
| WO | WO 2015/077794 A1 | 5/2015 |
| WO | WO 2015/095241 A2 | 6/2015 |
| WO | WO 2015/124637 A1 | 8/2015 |
| WO | WO 2016/133450 A1 | 2/2016 |
| WO | WO 2016/183577 A1 | 11/2016 |
| WO | WO 2016/191356 A1 | 12/2016 |
| WO | WO 2017/075098 A1 | 5/2017 |
| WO | WO 2017/152137 A2 | 9/2017 |

OTHER PUBLICATIONS

"ARGF—'Autologous Rehabilitation of Gastrointestinal Flora,'" Medipex Report for Medilink NW, pp. 1-42, n.d., Web, Feb. 10, 2012 <http://www.bacteriotherapy.org/docs/medipex-report. pelf>.

"Frequently Asked Questions about Clostridium difficile for Healthcare Providers," Healthcare-associated Infections (HAis), Centers for Disease Control and Prevention, pp. 1-6, Nov. 25, 2010, updated Mar. 6, 2012, Web, May 19, 2014 <http://www.cdc.gov/HAI/organisms/cdiff/Cdiff faqs HCP.html>.

"Functional Anatomy of Prokaryotic and Eukaryotic Cells," printed Mar. 16, 2017 <http://classes.midlandstech.edu/carterp/courses/bio225/chap04/lecture2.htm>.

"Monilia," Def. 1, Stedman's Medical Dictionary, n.d., Web, Nov. 22, 2005.

"Probiotic," Def. 1, MSN Encarta—Dictionary, Encarta, n.d., Web, Dec. 1, 2005.

Aas et al., "Recurrent Clostridium difficile Colitis: Case Series Involving 18 Patients Treated with Donor Stool Administered via a Nasogastric Tube," *Clinical Infectious Diseases*, 36(5):580-585 (2003).

Abrams, "Open-Label, Uncontrolled Trial of Bowel Sterilization and Repopulation with Normal Bowel Flora for Treatment of Inflammatory Bowel Disease," *Current Therapeutic Research*, 58(12):1001-1012 (1997).

Acha et al., "Changes of viability and composition of the *Escherichia coli* flora in faecal samples during long time storage," Journal of Microbiological Methods, Elsevier, 63(3):229-238 (2005).

Agrawal et al., "'Global warming' to *Mycobacterium avium* subspecies *paratuberculosis*," *Future Microbial*, 9(7):829-832 (2014).

Agrawal et al., "A Long-Term Follow-Up Study of the Efficacy and Safety of Fecal Microbiota Transplant (FMT) for Recurrent/Severe/Complicated *C. difficile* Infection (CDI) in the Elderly," *Gastroenterol*, 146(5)(Suppl 1):S42-43 (2014).

Aitken et al., "Demonstration of Intracellular *Mycobacterium* Species in Crohn's Disease Using Novel Technologies," Poster Presentation—2015 ACG Annual Scientific Meeting, Honolulu, Hawaii, USA (2015).

Akao et al., "A Purgative Action of Barbaloin Is Induced by *Eubacterium* sp. Strain BAR, a Human Intestinal Anaerobe, Capable of Transforming Barbaloin to Aloe-EmodinAnthrone," Biol. Pharm., 19(1):136-138 (1996).

Al-Eidan et al., "Clostridium difficile-associated diarrhoea in hospitalised patients," *J Clin. Pharm. Ther.*, 25(2):101-109 (2000).

Al-Nassir et al., "Comparison of Clinical and Microbiological Response to Treatment of Clostridium difficile-Associated Disease with Metronidazole and Vancomycin," *Clin Infect Dis.*, 47(1):56-62 (2008).

Anand et al., "Epidemiology, clinical manifestations, and outcome of Clostridium difficile-associated diarrhea," *Am J Gastroenterol.*, 89(4):519-23 (1994).

Ananthakrishnan et al., "Excess hospitalisation burden associated with Clostridium difficile in patients with inflammatory bowel disease," *Gut*, 57(2):205-210 (2007).

Anderson et al., "Systematic review: faecal microbiota transplantation in the management of inflammatory bowel disease," *Aliment. Pharmacol. Ther.*, 36:503-16 (2012).

Andoh et al., "Terminal restriction fragment polymorphisum analyses of fecal microbiota in five siblings including two with ulcerative colitis," *Journal of Clinical Gastroenterology*, 2:343-345 (2009).

Andeweg et al., "Guidelines of Diagnostic and Treatment of Acute Left-Sided Colonic Diverticulitis," Digestive Surgery 30:278-292 (2013).

Andrews et al., "'Putting back the bugs': Bacterial Treatment Relieves Chronic Constipation and Symptoms of Irritable Bowel Syndrome," *Med. J Aust.*, 159(9):633-634 (1993).

Andrews et al., "Bacteriotherapy for Chronic Constipation—a Long Term Follow-Up," *Gastroenterol*, 108:A563 Abstract (1995).

Andrews et al., "Chronic Constipation (CC) may be reversed by Bacteriotherapy," *Gastroenterol*, 106:A459 (1994).

Andrews et al., "Chronic constipation reversed by restoration of bowel flora. a case and a hypothesis," *European Journal of Gastroenterology & Hepatology*, 4:245-247 (1992).

Anorexia nervosa, Encyclopedia Index A, health AtoZ, Medical Network, Inc., pp. 1-7, n.d., Web, Nov. 23, 2005 <http://www.healthatoz.com/healthatoz/Atoz/ency/anorexia_nervosa.jsp>.

Arkkila et al., "Fecal Bacteriotherapy for Recurrent *Clostridium difficile* Infection," *Gastroenterology*, 138(5):SI-S5 (2010).

Aroniadis et al., "Intestinal Microbiota and the Efficacy of Fecal Microbiota Transplantation in Gastrointestinal Disease," Gastroenterology and Hepatology, 10(4):230-7 (2014).

Aroniadis et al., "Long-Term Follow-up Study of Fecal Microbiota Transplantation (FMT) for Severe or Complicated *Clostridium difficile* Infection (CDI)," *Gastroenterol*, 144(Suppl 1):S185 (2013).

Atarashi et al., "Induction of Colonic Regulatory T Cells by Indigenous *Clostridium* Species," *Science*, 331(6015):337-341, published online Dec. 23, 2010.

Atarashi et al., "$T_{reg}$ induction by a rationally selected mixture of *Clostridia* strains from the human microbiota," *Nature*, 500(7461):232-236 (2013).

Atarashi et al., "WS/PP-064-03 Regulation of colonic regulatory T cells by *Clostridium* species," *International Immunology*, 22(Suppl 1, Part 3), pp. 1-3 (2010).

Atarashi et al., WS-064 Mucosal immunity: homeostasis, 14th ICIC Abstract book, 14th International Congress of Immunology, pp. iii131-iii133 (2010).

(56) References Cited

OTHER PUBLICATIONS

Autism, Health Encyclopedia—Diseases and Conditions, the Health Scout Network, pp. 1-5, n.d., Web, Nov. 22, 2005 <www.healthscout.com>.
Autism, Treatment, Prognosis, Healthcommunities.com, Inc., pp. 1-4, n.d., Web. Jan. 28, 2009 <http://www.neurologychannel.com/common/PrintPage.php>.
Autism: Mayo Clinic.com, Mayo Foundation for Medical Education and Research, pp. 1-7, May 31, 2008, Web. Jan. 28, 2009 <http://www.mayoclinic.com/print/autism/DS00348/METHOD=print&DSECTION=all>.
Backhed et al., "Host-bacterial mutualism in the human intestine," *Science*, 307(5717):1915-1920 (2005).
Backhed et al., "Mechanisms underlying the resistance to diet-induced obesity in germ-free mice," *PNAS USA*, 104(3):979-984 (2007).
Backhed et al., "The gut microbiota as an environmental factor that regulates fat storage," *PNAS USA*, 101(44):15718-15723 (2004).
Bakken et al., "Fecal bacteriotherapy for recurrent Clostridium difficile infection," *Anaerobe*, 15(6):285-289 (2009).
Bakken et al., "Treating Clostridium difficile Infection with Fecal Microbiota Transplantation," *Clinical Gastroenterology and Hepatology*, 9(12):1044-1049 (2011).
Bartlett et al., "Clinical recognition and diagnosis of Clostridium difficile infection," *Clin Infect Dis.*, 46(Suppl 1):S12-S18 (2008).
Bartlett, "Clostridium difficile-associated Enteric Disease," *Curr Infect Dis Rep.*, 4(6):477-483 (2002).
Belkaid et al., "Natural regulatory T cells in infectious disease," *Nature Immunology*, 6(4):353-360 (2005).
Bengmark et al., "Bioecological control of inflammatory bowel disease," *Clinical Nutrition*, 26(2):169-181 (2007).
Bennet et al., "Treatment of ulcerative colitis by implantation of normal colonic flora," *Lancet*, 333(8630):164 (1989).
Benson et al., "Changing epidemiology of Clostridium difficile-associated disease in children," *Infect Control Hosp Epidemiol.*, 28(11):1233-1235 (2007).
Bergey's Manual of Systematic Bacteriology, Second Edition, vol. Three, The Firmicutes, pp. 1-16 (2009).
Blaser et al., "What are the consequences of the disappearing human microbiota?" *Nat. Rev. Microbial.*, 7(12):887-894 (2009).
Blaser, "Who are we? Indigenous microbes and the ecology of human diseases," *EMBO Rep*, 7(10):956-960 (2006).
Bolte, "Autism and Clostridium tetani," Medical Hypotheses, 51(2):133-144 (1998).
Bolte, Therapies for Gastrointestinal and Neurological Disorders, U.S. Appl. No. 60/214,813, filed Jun. 28, 2000.
Borody et al., "Fecal microbiota transplantation in gastrointestinal disease: 2015 update and the road ahead," Expert Review of Gastroenterology and Hepatology, 9(11):1379-1391 (2015).
Borody et al., "Anti-MAP Rescues Anti-TNF Failures for Over 4 Years," *Gastroenterol*, 136(5)Suppl 1:A-681 (2009).
Borody et al., "Anti-MAP Therapy for Pediatric Crohn's Disease," *Am J Gastroenterol*, 108(Suppl 1):S516 (2013).
Borody et al., "Anti-MAP Therapy in the Treatment of Active Crohn's Disease," *J Gastroenterol & Hepatol*, 20(Suppl):A2 (2005).
Borody et al., "Anti-mycobacterial therapy in Crohn's disease heals mucosa with longitudinal scars," *Digestive & Liver Disease*, 39(5):438-444 (2007).
Borody et al., "Anti—*Mycobacterium avium* SS *Paratuberculosis* (MAP) Therapy and Fistula Closure in Patients with Severe Crohn's Disease," *Am J Gast*, Al 0J:5440 (2006).
Borody et al., "Bacteriotherapy in Chronic Fatigue Syndrome (CFS): a retrospective review," *AmJGastro*, 107(SJ):A1481 (2012).
Borody et al., "Bacteriotherapy Using Fecal Flora: toying with human motions" *J Clin. Gastroenterol.*, 38(6):475-483 (2004).
Borody et al., "Bowel-flora alteration: a potential cure for inflammatory bowel disease and irritable bowel syndrome?" *Med. J Aust.*, 150:604 (1989).

Borody et al., "Changes in Crohn's Disease Activity Index and C-Reactive Protein Levels During Anti-MAP Therapy," *AM J Gastro*, 104(S3):A1293 (2009).
Borody et al., "*Clostridium difficile* Complicating Inflammatory Bowel Disease: Pre- and Post-Treatment Findings," *Gastroenterol*, 134(4)Suppl 1:A-361 (2008).
Borody et al., "Could fecal microbiota transplantation cure all Clostridium difficile infections?," *Future Microbial*, 9:1-3 (2014).
Borody et al., "*Entamoeba histolytica*: another cause of Crohn's Disease," *AM J Gastro*, 104(S3):A990 (2009).
Borody et al., "Faecal bacteriotherapy (FB) for chronic *C. difficile* (Cd) syndromes," *J Gastroenterol Hepatol*,18(Suppl.):B8 (Abstract) (2003).
Borody et al., "Fecal bacteriotherapy in the treatment of recurrent C. difficile infection," *UpToDate*, pp. 1-6 (2006).
Borody et al., "Fecal Microbiota Transplantation (FMT) in Multiple Sclerosis (MS)," *AMJGastro*, 106(S2):A942 (2011).
Borody et al., "Fecal microbiota transplantation and emerging applications," *Nat. Rev. Gastroenterol. Hepatol.*, 9(2):88-96 (2011).
Borody et al., "Fecal microbiota transplantation for *Clostridium difficile* infection: a surgeon's perspective" *Seminars in Colon and Rectal Surgery*, 25:163-166 (2014).
Borody et al., "Fecal microbiota transplantation in gastrointestinal diseases—What practicing physicians should know," *Polish Archives of Internal Medicine*, 125(11):852-858 (2015).
Borody et al., "Fecal microbiota transplantation in the treatment of recurrent Clostridium difficile infection," *UpToDate*, pp. 1-4, (2015).
Borody et al., "Fecal Microbiota Transplantation in Ulcerative Colitis: Review of 24 Years Experience," *Am J Gastro*, 107(Supp 1):A1644 (2012).
Borody et al., "Fecal microbiota transplantation: a new standard treatment option for *Clostridium difficile* infection," *Expert Rev Anti Infect Ther.*, 11(5):447-449 (2013).
Borody et al., "Fecal microbiota transplantation: current status and future directions," *Expert Review of Gastroenterology & Hepatology*, 5(6):653-655 (2011).
Borody et al., "Fecal Microbiota Transplantation: Expanding Horizons for *Clostridium difficile* Infections and Beyond," *Antibiotics*, 4:254-266 (2015).
Borody et al., "Fecal Microbiota Transplantation: Indications, Methods, Evidence, and Future Directions," *Curr Gastroenterol Rep*, 15:337-344 (2013).
Borody et al., "Fecal Microbiota Transplantation: Techniques, Applications, and Issues," *Gastroenterol Clin North Am*, 41:781-803 (2012).
Borody et al., "Irritable Bowel Syndrome and *Dientamoeba fragilis*," *ASM Sydney National Conference*, pp. 4-5 (2002).
Borody et al., "Is Crohn's Disease Ready for Fecal Microbiota Transplantation?," *J Clin Gastroenterol*, 48(7):582-583 (2014).
Borody et al., "Myoclonus-dystonia affected by GI Microbiota?," *AM J Gastro*, 106(S2):A940 (2011).
Borody et al., "Novel appearance of healing mucosa following anti-*Mycobacterium avium paratuberculosis* therapy for Crohn's disease," *J Gastroenterol Hepatol*, 19(Suppl):A210 (2004).
Borody et al., Reversal of Idiopathic Thrombocytopenic Purpura [ITP] with Fecal Microbiota Transplantation [FMT], *AM J Gastro*, 106(S2):A941 (2011).
Borody et al., "Reversal of Inflammatory Bowel Disease (IBD) with Recurrent Faecal Microbiota Transplants (FMT)," *AM J Gastro*, 106(S2):A979 (2011).
Borody et al., "Severe recurrent Crohn's Disease of ileocolonic anastomosis and antimicrobial (anti-mycobacterial therapy)," *Gut*, 55:1211 (2006).
Borody et al., "The GI Microbiome and its Role in Chronic Fatigue Syndrome: a Summary of Bacteriotherapy," ACNEM Journal, 31(3):3-8 (2012).
Borody et al., "Therapeutic faecal microbiota transplantation: current status and future developments," *Curr Opin Gastroenterol*, 30:97-105 (2014).
Borody et al., "Treatment of chronic constipation and colitis using human probiotic infusions," *Proceedings of Prebiotics and Probiotics and the New Foods Conference*, 2-4:228 Abstract (2001).

(56) References Cited

OTHER PUBLICATIONS

Borody et al., "Treatment of First-time Clostridium difficile Infection with Fecal Microbiota Transplantation," Poster Presentation, *2015 ACG Annual Scientific Meeting*, Honolulu, Hawaii, USA (2015).
Borody et al., "Treatment of Severe Constipation Improves Parkinson's Disease (PD) Symptoms," *AM J Gastro*, 104(S3):A999 (2009).
Borody et al., "Treatment of Severe Crohn's Disease (CD)—Using Rifabutin-Macrolide-Clofazimine Combination: Results at 30-37 Months," *Gastroenterology*, 118(4):A1334 Abstract (2000).
Borody et al., Treatment of Severe Crohn's Disease Using Rifabutin-Macrolide-Clofazimine Combination—Results at 38-43 Months, *J Gastroenterol & Hepatol*, 15(Suppl.):J102 (2000).
Borody et al., "Treatment of Severe Crohn's disease using antimycobacterial triple therapy—approaching a cure?," *Digest Liver Dis*, 34(1):29-38 (2002).
Borody et al., "Treatment of ulcerative colitis using fecal bacteriotherapy," *J Clin. Gastroenterol.*, 37(1):42-47 (2003).
Borody, "Bacteriotherapy for Chronic Fatigue Syndrome—a Long Term Follow-Up Study," Proceedings of ACMA Complementary Medicine Sydney, p. 1 (1995).
Borody, "Flora Power—Fecal Bacteria Cure Chronic C. difficile Diarrhoea," *Am J Gastroenterol*, 95(11):3028-3029 (2000).
Borody, "Is the Infected Patient too 'Difficile' to Treat?," The Australian Society for Microbiology 2009 Perth, SY03 & SY03. 1, p. 27 & 56, (2009).
Borody, "Letter to the Editor—Response to Drs. Famularo et al.,"*AJG*, 96(7):2262-2264 (2001).
Borriello, "Clostridial Disease of the Gut" Clinical Infectious Diseases, The University of Chicago, 20(Suppl 2):S242-S250 (1995).
Bowden et al., "Pseudomembraneous enterocolitis: mechanism of restoring floral homeostasis," *Am Surg.*, 47(4):178-183 (1981).
Brandt et al., "Endoscopic Fecal Microbiota Transplantation: "First-Line" Treatment for Severe Clostridium difficile Infection?" *J Clin. Gastroenterol.*, 45(8):655-657 (2011).
Brandt et al., "Fecal microbiota transplantation for recurrent *Clostridium difficile* infection," *JClin Gastroenterol.*, 45(Suppl):S159-S167 (2011).
Brandt et al., "Long-Term Follow-Up Study of Fecal Microbiota Transplantation (FMT) for Ulcerative Colitis (UC)," *Am. J. Gastroenterol.*, 107(Suppl 1):S657 (2012).
Brandt et al., Safety of Fecal Microbiota Transplantation (FMT) in Immunocompromised (le) Patients with Inflammatory Bowel Disease (IBD), *Am J Gastroenterol*, 108(Suppl 1):S556 (2013).
Browne et al., "Culturing of 'unculturable' human microbiota reveals novel taxa and extensive sporulation," *Nature*, 533(7604):543-546 (2016).
Bueche et al., "Quantification of Endospore-Forming *Firmicutes* by Quantitative PCR with the Functional Gene spo0A," *Applied and Environmental Microbiology*, 79(17):5302-5312 (2013).
Cammarota et al., "Randomised clinical trial: faecal microbiota transplantation by colonoscopy vs. vancomycin for the treatment of recurrent Clostridium difficile infection," Alimentary Pharmacology & Therapeutics, 41(9):835-843 (2015).
Cammorata et al., "Review article: biofile formation by Helicobacter pylori as a target for eradication of resistant infection," Aliment Pharmacol Ther, 36:222-30 (2012).
Campbell et al., "The many faces of Crohn's Disease: Latest concepts in etiology," *OJIM*, 2(2):107-115 (2012).
Cano et al., "Revival and identification of bacterial spores in 25-40 million year old Dominican Amber Science," Science, 268(5213):1060-1064 (1995).
Cato et al., "*Clostridium oroticum* comb. nov. amended description," *International Journal of Systematic Bacteriology*, 17(1):9-13 (1968).
Celik et al., "Factors influencing the stability of freeze-dried stress-resilient and stress-sensitive strains of bifidobacteria," J. Dairy Sci., 96(6):3506-16 (2013).
Center for Disease Control, "Severe Clostridium difficile-associated disease in populations previously at low risk—four states, 2005." *Morbidity and Mortality Weekly Report*, 54(47):1201-1205 (2005).

Chamberlain et al., "MAP-associated Crohn's Disease, MAP, Koch's postulates, causality and Crohn's Disease," *Digestive and Liver Disease*, 39:790-794 (2007).
Chamberlin et al., "Primary treatment of Crohn's disease: combined antibiotics taking center stage," *Expert Rev. Clin. Immunol.*, 7(6):751-760 (2011).
Chang et al., "Decreased diversity of the fecal Microbiome in recurrent Clostridium difficile-associated diarrhea," *J Infect. Dis.*, 197(3):435-438 (2008).
Chen et al., "A mouse model of Clostridium difficile-associated disease," *Gastroenterology*, 135(6):1984-1992 (2008).
Cherif et al., "Thuricin 7: a novel bacteriocin produced by Bacillus thuringiensis BMG1.7, a new strain isolated from soil," Letters in Applied Microbiology, 32:243-7 (2001).
Chibani-Chennoufi et al., "In Vitro and In Vivo Bacteriolytic Activities of *Escherichia coli* Phages: Implications for Phage Therapy," *Antimicrobial Agents and Chemotherapy*, 48(7):2558-2569 (2004).
Choi et al., "Fecal Microbiota Transplantation: Current Applications, Effectiveness, and Future Perspectives," Clin. Endosc., 49:257-265 (2016).
Chopra et al., "Recent epidemiology of Clostridium difficile infection during hematopoietic stem cell transplantation," *Clin Transplant.*, 25(1):E82-E87 (2011).
Chu et al., "Profiling Living Bacteria Informs Preparation of Fecal Microbiota Transplantations," *PLoS One*, 1-16 (2017).
Citron et al., "In Vitro Activities of CB-183,315, Vancomycin, and Metronidazole against 556 Strains of *Clostridium difficile*, 445 Other Intestinal Anaerobes, and 56 *Enterobacteriaceae* Species," *Antimicrob Agents Chemother.*, 56(3):1613-1615 (2012).
Claesson et al., "Comparison of two next-generation sequencing technologies for resolving highly complex microbiota composition using tandem variable 16S rRNA gene regions," *Nucleic Acids Research*, 38(22):1-13 (2010).
Clancy et al., "Anti-MAP Therapy Induces and Maintains Remission in Severe Crohn's Disease," *Ann NY Acad Sci*, p. 1 (2005).
Claus et al., "Colonization-induced host-gut microbial metabolic interaction," *MBio*, 2(2):e00271-00210 (2011).
Claus et al., "Systemic multicompartmental effects of the gut microbiome on mouse metabolic phenotypes," *Mal. Syst. Biol.*, 4(1):219 (2008).
Cohen et al., "Clinical practice guidelines for Clostridium difficile infection in adults: 2010 update by the society for healthcare epidemiology of America (SHEA) and the infectious diseases society of America (IDSA)," *Infect Control Hosp Epidemiol.*, 31(5):431-55 (2010).
Collins et al., "The Phylogeny of the Genus *Clostridium*: Proposal of Five New Genera and Eleven New Species Combinations," *International Journal of Systematic Bacteriology*, pp. 812-826 (1994).
U.S. Appl. No. 12/843,409, filed Jul. 26, 2010.
Crohn's Disease, Prevention, Health Guide A-Z, WebMDHealth, pp. 1-2, n.d., Web, Oct. 23, 2005 <http://mywebmd.com/hw/inflammatory.sub.--bowel/uf6012.asp>.
Crowther, "Transport and Storage of Faeces for Bacteriological Examination," Journal of Applied Bacteriology, 34(2):477-483 (1971).
Cutolo et al., "Fecal feedings as a therapy in *Staphylococcus enterocolitis*," *NY State J Med*, 59:3831-3833 (1959).
Dale et al., "Molecular interactions between bacterial symbionts and their hosts," *Cell*, 126(3):453-465 (2006).
Dan et al., "Comparison of preservation media and freezing conditions for storage of specimens of faeces," J. Med Microbiology, 28:151-154 (1989).
De Giulio et al., "Use of Alginate and Cryo-Protective Sugars to Improve the Viability of Lactic Acid Bacteria After Freezing and Freeze-Drying," World Journal of Microbiology & Biotechnology, 21:739-746 (2005).
Defang et al., "In vitro and in vivo evaluation of two extended release preparations of combination metformin and glipizide," *Drug Develop. & Indust. Pharm.*, 31:677-685 (2005).
Definition of Kit, Merriam-Webster, pp. 1-10., Web., 2019 <https://www.merriam-webster.com/dictionary/kit>.

(56) References Cited

OTHER PUBLICATIONS

Dendukuri et al., "Probiotic therapy for the prevention and treatment of Clostridium difficile-associated diarrhea: a systematic review," *CMAJ*, 173(2):167-170 (2005).
Derwent Abstract Accession No. 98-230427/20, WO 98/13068 A, (Kuperman VB) Apr. 2, 1998.
Dethlefsen et al., "An ecological and evolutionary perspective on human-microbe mutualism and disease," *Nature*, 449(7164):811-818 (2007).
Dewhirst et al., "Phylogeny of the Defined Murine Microbiota: Altered Schaedler Flora," *Applied and Environmental Microbiology*, 65(8):3287-3292 (1999).
DuPont, "The search for effective treatment of Clostridium difficile infection," *N Engl J Med.*, 364(5):473-475 (2011).
Eckburg et al., "Diversity of the human intestinal microbial flora," *Science*, 308(5728):1635-1638 (2005).
Eiseman et al., "Fecal enema as an adjunct in the treatment of pseudomembranous enterocolitis," *Surgery*, 44(5):854-859 (1958).
Eller et al., "Anaerobic Roll Tube Media for Nonselective Enumeration and Isolation and Bacteria in Human Feces," *Applied Microbiology*, 22(4):522-529 (1971).
Extended European Search Report dated Apr. 3, 2014, in European Patent Application No. 11813951.8.
Extended European Search Report dated Mar. 16, 2018, in European Patent Application No. 17203052.0.
Extended European Search Report dated Nov. 30, 2016, in European Patent Application No. 16193790.9.
Faust et al., "Treatment of recurrent pseudomembranous colitis (RPMC) with stool transplantation (ST): Report of six (6) cases," *Can J Gastroenterol.*, 16:A43 (2002).
Fenton et al., "Pseudomembranous colitis associated with antibiotic therapy—an emerging entity," *Can Med Assoc J*, 111(10):1110-1111 (1974).
Floch et al., "Probiotics and Dietary Fiber, the Clinical Coming of Age of Intestinal Microecology," J. Clin. Gastroenterology, 27(2):99-100 (1998).
Floch, "Fecal Bacteriotherapy, Fecal Transplant, and the Microbiome," J. Clin. Gastroenterol., 44(8):529-530 (2010).
Flotterod et al., "Refractory Clostridium difficile infection. Untraditional treatment of antibiotic-induced colitis," *Tidsskr Nor Laegeforen*, 111:1364-1365 (1991).
Frank et al., "Molecular-phylogenetic characterization of microbial community imbalances in human inflammatory bowel diseases," *PNAS*, 104(34):13780-13785 (2007).
Frantzen et al., "Empirical evaluation of preservation methods for faecal DNA," *Molecular Ecology*, 7(10):1423-1428 (1998).
Freeman et al., "The changing epidemiology of Clostridium difficile infections," *Clin Microbial. Rev.*, 23(3):529-549 (2010).
Frese et al., "The evolution of host specialization in the vertebrate gut symbiont Lactobacillus reuteri," *PloS Genet.*, 7(2):e1001314 (2011).
Gaboriau-Routhiau et al., "The Key Role of Segmented Filamentous Bacteria in the Coordinated Maturation of Gut Helper T Cell Responses," *Immunity*, 31(4):677-689 (2009).
Garborg et al., "Results of faecal donor instillation therapy for recurrent Clostridium difficile-associated diarrhoea," *Scand J Infect Dis.*, 42(11-12):857-61 (2010).
Garey et al., "Meta-analysis to assess risk factors for recurrent Clostridium difficile infection," *J. Hosp. Infect.*, 70(4):298-304 (2008).
Gerding, "Management of Clostridium difficile infection: thinking inside and outside the box," *Clin Infect Dis.*, 51(11):1306-13 (2010).
Geuking et al., "Intestinal Bacterial Colonization Induces Mutualistic Regulatory T Cell Responses," *Immunity*, 34:794-806 (2011).
Gitlin et al., "*Mycobacterium avium* ss *paratuberculosis*-associated Diseases: Piecing the Crohn's Puzzle Together," *J Clin Gastroenterol*, 46(8):649-655 (2012).
Gough et al., "Systematic review of intestinal microbiota transplantation (fecal bacteriotherapy) for recurrent Clostridium difficile infection," *Clin. Infect. Dis.*, 53(10):994-1002 (2011).
Grehan et al., "Durable alteration of the colonic microbiota by the administration of donor fecal flora," *Journal of Clinical Gastroenterology*, 44(8):551-561 (2010).
Guarner et al., "Gut flora in health and disease," *Lancet*, 361(9356):512-519 (2003).
Gustafsson et al., "The Effect of Faecal Enema on Five Microflora-Associated Characteristics in Patients with Antibiotic-Associated Diarrhoea," *Scandinavian Journal of Gastroenterology*, 34:580-586 (1999).
Gustafsson et al., "Faecal Short-Chain Fatty Acids in Patients with Antibiotic-Associated Diarrhoea, before and after Faecal Enema Treatment," *Scand J Gastroenterol*, 33:721-727 (1998).
Hamilton et al., "Change in microbial community composition of in patients with recalcitrant Clostridium difficile colitis treated with fecal bacteriotherapy," International Human Microbiome Congress, Poster and Presentation, Vancouver, ON, Canada, Mar. 9-11, 2011.
Hamilton et al., "High-throughput DNA sequence analysis reveals stable engraftment of gut microbiota following transplantation of gut microbiota following transplantation of previously frozen fecal bacteria," *Gut Microbes*, 4(2):1-11 (2013).
Hamilton et al., "Standardized Frozen Preparation for Transplantation of Fecal Microbiota for Recurrent Clostridium difficile Infection," Article and Supplementary Material, *Am. J. Gastroenterol.*, 107(5):761-767 (2012).
Hayashi et al., "Phylogenetic Analysis of the Human Gut Microbiota Using 16S rDNA Clone Libraries and Strictly Anaerobic Culture-Based Methods," *Microbial. Immunol.*, 46(8):535-548 (2002).
Hecker et al., "Fecal Microbiota Transplantation by Freeze-Dried Oral Capsules for Recurrent Clostridium difficile Infection," *Open Forum Infect Dis*, 3(2): 1-2 (2016).
Hellemans et al., "Fecal transplantation for recurrent Clostridium difficile colitis, an underused treatment modality," *Acta Gastroenterol Belg.*, 72(2):269-70 (2009).
Henriksson et al., "Probiotics under the regulatory microscope," *Expert Opin. Drug Saf*, 4(6):1-9 (2005).
Hensel et al., "Vagal Ascent and Distribution of 125 I-Tetanus Toxin after Injection into the Anterior Wall of the Stomach," Naunyn-Schmiedeberg's Arch. Pharmacol, 276:395-402 (1973).
Honda et al., "Regulation of T Cell Responses by Intestinal Commensal Bacteria," *Journal of Intestinal Microbiology*, vol. 25, 2nd Edition:104 (2011).
Hongliang et al., "Freeze-dried, Capsulized Fecal Microbiota Transplantation for Relapsing Clostridium difficile Infection," *Journal of Clinical Gastroenterology*, 43(6):537-538 (2015).
Hooper et al., "How host-microbial interactions shape the nutrient environment of the mammalian intestine," *Annu. Rev. Nutr.*, 22:283-307 (2002).
Hope et al., "Sporadic colorectal cancer-role of the commensal microbiota," *FEMS Microbial. Lett.*, 244:1-7 (2005).
Hota et al., "Determining Mortality Rates Attributable to Clostridium difficile Infection," *Emerg. Infect. Dis.*, 18(2):305-307 (2012).
Hota et al., "Oral Vancomycin Followed by Fecal Transplant Versus Tapering Oral Vancomycin," U.S. National Institutes of Health, Clinical Study No. NCT01226992, Oct. 20, 2010, last updated Jan. 14, 2013, Web, May 20, 2014, pp. 1-4 <http://clinicaltrials.gov/ct2/show/NCT01226992>.
Hsu et al., "IL-10 Potentiates Differentiation of Human Induced Regulatory T Cells via STAT3 and Foxo1," *The Journal of Immunology*, 3665-3674 (2015).
Hu et al., "Prospective derivation and validation of a clinical prediction rule for recurrent Clostridium difficile infection," *Gastroenterology*, 136:1206-1214 (2009).
Huang et al., "Once-daily propranolol extended-release tablet dosage form: formulation design and in vitro/in vivo investigation," *European J of Pharm. & Biopharm.*, 58:607-614 (2004).
Huttenhower et al., "Structure, function and diversity of the healthy human microbiome," The Human Microbiome Project Consortium, *Nature*, 486:207-214 (2012).
Immunology in the 21st Century: Defeating Infection, Autoimmunity, Allergy, and Cancer, ICI 2010 Wrap-up Report, 14th International Congress of Immunology, pp. 1 (2010).
Inflammatory Bowel Disease Facts, Disease Prevention and Treatment Strategies, Crohn's Disease and Inflammatory Bowel Disease

(56) References Cited

OTHER PUBLICATIONS (IBD), HealingWithNutrition.com, pp. 1-4, n.d., Web, Oct. 23, 2005 <http://www.HealingWithNutrition.com/disease/inflambowel/chrohns.html>.
Information Disclosure Statement filed Nov. 28, 2017, in U.S. Appl. No. 15/487,553.
International Preliminary Examination Report dated Nov. 19, 2002, in International Application No. PCT/AU2001/000907, 19 pgs.
International Preliminary Report on Patentability dated Dec. 12, 2012, in International No. PCT/AU2011/000987, 35 pgs.
International Preliminary Report on Patentability dated Mar. 12, 2015, in International Application No. PCT/AU2013/001362, 29 pgs.
International Preliminary Report on Patentability dated Sep. 10, 2013, in International Application No. PCT/US2012/028484, 10 pgs.
International Search Report and Written Opinion (WO) dated Feb. 2, 2018 in International Application No. PCT/US2017 /055618.
International Search Report and Written Opinion (WO) dated Feb. 2, 2018 in International Application No. PCT/US2017/056131.
International Search Report and Written Opinion (WO) dated Feb. 21, 2018 in International Application No. PCT/US2017/056129.
International Search Report and Written Opinion (WO) dated Jan. 17, 2018, in International Application No. PCT/US2017 /045092.
International Search Report and Written Opinion (WO) dated Jan. 31, 2018 in International Application PCT/US2017/056126.
International Search Report and Written Opinion dated Aug. 17, 2018, in International Application No. PCT/US2018/034673.
International Search Report and Written Opinion dated Aug. 2, 2018, in International Application No. PCT/US2018/026074.
International Search Report and Written Opinion dated Jul. 30, 2018, in International Application No. PCT/US2018/026080.
International Search Report and Written Opinion dated Aug. 8, 2016, in International Application No. PCT/US2016/032695, 10 pgs.
International Search Report and Written Opinion dated Feb. 5, 2014, in International Application No. PCT/AU2013/001362, 17 pgs.
International Search Report and Written Opinion dated Jan. 5, 2017, in International Application No. PCT/US2016/058938.
International Search Report and Written Opinion dated Jul. 31, 2014, in International Application No. PCT/US2014/027391, 16 pgs.
International Search Report and Written Opinion dated Oct. 28, 2011, in International No. PCT/AU2011/000987, 18 pgs.
International Search Report dated Aug. 10, 2012, in International Application No. PCT/US2012/028484, 7 pgs.
International Search Report dated Jul. 29, 2014, in International Application No. PCT/AU2014/000478, 7 pgs.
International Search Report dated Sep. 22, 2017, in International Application No. PCT/US2017/040591, 12 pgs.
Irrgang et al., "The historical Development ofMutaflor therapy," Ardeypharm GmbH, pp. 1-38 (1988) <http://www.ardeypharm.de/pdfs/en/mutaflor_historical_e.pdf?>.
Irritable Bowel Syndrome (IBS), Health A to Z, InteliHealth, pp. 1-4, n.d., Web, Oct. 23, 2005 <http://www.intelihealth.com>.
Issa et al., "Clostridium difficile and Inflammatory Bowel Disease," *Inflamm Bowel Dis.*, 14(10):1432-1442 (2008).
Issa et al., "Impact of Clostridium difficile on inflammatory bowel disease," *Clin. Gastroenterol. Hepatol.*, 5(3):345-351 (2007).
Itoh et al., "Characterization of clostridia isolated from faeces of limited flora mice and their effect on caecal size when associated with germ-free mice," *Laboratory Animals*, 19:111-118 (1985).
Itoh et al., "Intestinal bacteria antagonistic to *Clostridium difficile* in mice," *Laboratory Animals*, 21:20-25 (1987).
Ivanov et al., "Specific Microbiota Direct the Differentiation of IL-17-Producing T-Helper Cells in the Mucosa of the Small Intestine," *Cell Host & Microbe*, 4:337-349 (2008).

Jacob et al., "Single Delivery of High-Diversity Fecal Microbiota Preparation by Colonoscopy Is Safe and Effective in Increasing Microbial Diversity in Active Ulcerative Colitis," *Inflamm Bowel Dis.*, 0(0):1-9 (2017).
Janeway et al., "Adaptive Immunity to Infection," *Immunobiology*, 6th Edition, Chapter 10, pp. 414 (2005).
Janeway, Jr. et al., "Autoimmune responses are directed against self antigens," *Immunobiology: the Immune System in Health and Disease*, 5th Edition, pp. 1-4 (2001).
Jarvis et al., "National point prevalence of Clostridium difficile in US health care facility inpatients, 2008," *Am. J. Infect. Control*, 37:263-270 (2009).
Johnson et al., "Interruption of Recurrent Clostridium difficile-Associated Diarrhea Episodes by Serial Therapy with Vancomycin and Rifaximin," *Clin. Infect. Dis.*, 44(6):846-848 (2007).
Johnson et al., "Rifaximin Redux: Treatment of recurrent Clostridium difficile infections with Rifaximin immediately post-vancomycin treatment," *Anaerobe*, 15(6):290-291 (2009).
Kageyama et al., "Emendation of genus *Collinsella* and proposal of *Collinsella stercoris* sp. nov. and *Collinsella intestinalis* sp. nov.," International Journal of Systematic and Evolutionary Microbiology, 50:1767-1774 (2000).
Kageyama et al., "Phylogenetic and phenotypic evidence for the transfer of Eubacterium aerofaciens to the genus *Collinsella* as *Collinsella aerofaciens* gen. nov., comb. nov.," International Journal of Systematic Bacteriology, 49:557-565 (1999).
Kakihana et al., "Fecal microbiota transplantation for patients with steriod-resistant acute graft-versus-host disease of the gut," *Blood*, 128(16):2083-2088 (2016).
Kamboj et al., "Relapse versus reinfection: surveillance of Clostridium difficile infection," *Clininfect Dis.*, 53(10):1003-1006 (2011).
Kang et al., "Microbiota Transfer Therapy alters gut ecosystem and improves gastrointestinal and autism symptoms: an open-label study," Microbiome, 5:10, 16 pages (2017).
Karas et al., "A review of mortality due to Clostridium difficile infection," *J Infect.*, 61(1): 1-8 (2010).
Kassam et al., "Fecal transplant via retention enema for refractory or recurrent Clostridium difficile infection," *Arch Intern Med.*, 172(2):191-193 (2012),
Kelly et al., "Commensal gut bacteria: mechanisms of immune modulation," *Trends in Immunology*, 26(6):326-333 (2005).
Kelly et al., "Clostridium difficile—more difficult than ever," *N. Engl. J. Med.*, 359(18):1932-1940 (2008).
Kelly et al., "Clostridium difficile colitis," *N Engl. J Med.*, 330(4):257-62 (1994).
Kelly et al., "Fecal Microbiota Transplant for Treatment of *Clostridium difficile* Infection in Immunocompromised Patients," *Am J Gastroenterol*, 109:1065-1071 (2014).
Kelly et al., "Fecal microbiota transplantation for relapsing Clostridium difficile infection in 26 patients: methodology and results," *J Clin. Gastroenterol.*, 46(2):145-149 (2012).
Keynan et al., "The Role of Regulatory T Cells in Chronic and Acute Viral Infections," *Clinical Infectious Diseases*, 46:1046-1052 (2008).
Khanna et al., "A Novel Microbiome Therapeutic Increases Gut Microbial Diversity and Prevents Recurrent Clostridium difficile Infection," The Journal of Infectious Diseases, 214:173-81 (2016).
Khanna et al., "The epidemiology of community-acquired Clostridium difficile infection: a population-based study," *Am J Gastroenterol.*, 107(1):89-95 (2012).
Khanna et al., "The growing incidence and severity of Clostridium difficile infection in inpatient and outpatient settings," *Expert Rev Gastroenterol Hepatol.*, 4(4):409-16 (2010).
Kharidia et al., "The Activity of a Small Lytic Peptide PTP-7 on *Staphylococcus aureus* Biofilms," *J Microbial.*, 49(4):663-668 (2011).
Khoruts et al., "Changes in the composition of the human fecal microbiome after bacteriotherapy for recurrent Clostridium difficile-associated diarrhea," *J Clin. Gastroenterol.*, 44(5):354-360 (2010).
Khomts et al., "Therapeutic transplantation of the distal gut microbiota," *Mucosa! Immunol.*, 4(1):4-7 (2011).

(56) References Cited

OTHER PUBLICATIONS

Kim et al., "Effect of Rifampin on the Plasma Concentration and the Clinical Effect of Haloperidol Concomitantly Administered to Schizophrenic Patients," Journal of Clinical Psychopharmacology, 16(3):247-252 (1996).
Kim et al., "In Vitro Culture Conditions for Maintaining a Complex Population of Human Gastrointestinal Tract Microbiota," Journal of Biomedicine and Biotechnology, 2011(Article ID 838040):1-10 (2011) <http://www.hindawi.com/journals/bmri/2011/838040/>.
Klaenhammer, "Bacteriocins of lactic acid bacteria," Biochimie, 70:337-49 (1988).
Klarenbeek et al., "Review of current classification for diverticular disease and a translation into clinical practice," *Int. J. Colorectal Dis* 27:207-214 (2012).
Kleiman et al., "Comparison of two coprological methods for the veterinary diagnosis of fasciolosis," *Arquivo Brasileiro de Medicina Veterinaria e Zootcenica*, 55(2):181-185 (2005).
Kobashi et al., "Metabolism of Sennosides by Human Intestinal Bacteria," Journal of Medicinal Plant Research, 40(3):225-236 (1980).
Koch, "What size should a bacterium be? a question of scale," Annu. Rev. Microbial., 50:317-48 (1996).
Krogius-Kurikka et al., "Sequence analysis of percent G+C fraction libraries of human faecal bacterial DNA reveals a high number of *Antinobacteria*," *BMC Microbiology*, 9(68):1-13 (2009).
Kuijper et al. "Update of Clostridium difficile Infection due to PCR Ribotype 027 in Europe, 2008," *Euro. Surveill.*, 13(31):Article 5 (2008).
Kuksal et al., "Formulation and In Vitro, In Vivo Evaluation of Extended-release Matrix Tablet of Zidovudine: Influence of Combination of Hydrophilic and Hydrophobic Matrix Formers," *AAPS Pharm.*, 7(1):E1-E9 (2006).
Kunde et al., "Safety, Tolerability, and Clinical Response After Fecal Transplantation in Children and Young Adults With Ulcerative Colitis," *JPNG*, 56(6):597-601 (2013).
Kyne et al., "Association between antibody response to toxin A and protection against recurrent Clostridium difficile diarrhea," *Lancet*, 357(9251):189-93 (2001).
Kyne et al., "Asymptomatic carriage of Clostridium difficile and serum levels of IgG antibody against toxin A," *N Engl J Med.*, 342(6):390-397 (2000).
Kyne et al., "Factors associated with prolonged symptoms and severe disease due to Clostridium difficile," *Age and Ageing*, 28(2):107-13 (1999).
Kysela et al., "Serial analysis of V6 ribosomal sequence tags (SARST-V6): a method for efficient, high-throughput analysis of microbial community composition," *Environmental Microbiology*, 7(3):356-364 (2005).
Labbe et al., "Clostridium difficile infections in a Canadian tertiary care hospital before and during a regional epidemic associated with the BI/NAP1/027 strain," *Antimicrob Agents Chemother.*, 52(9):3180-7 (2008).
Lamontagne et al., "Impact of emergency colectomy on survival of patients with fulminant Clostridium difficile colitis during an epidemic caused by a hypervirulent strain," *Ann. Surg.*, 245(2):267-272 (2007).
Larsen et al., "Gut Microbiota in Human Adults with Type 2 Diabetes Differs from Non-Diabetic Adults," PLoS One, 5(2): e9085-e9095 (2010).
Lau et al., "Bacteraemia caused by *Anaerotruncus colihominis* and emended description of the species," *JClin Pathol*, 59:748-752 (2006).
Lawson et al., "*Anaerotruncus colihominis* gen. nov., sp. nov., from human faeces," *International Journal of Systematic and Evolutionary Microbiology*, 54:413-417 (2004).
Lawson et al., "Anaerotruncus," *Bergey's Manual of Systematics of Archae and Bacteria*, pp. 1-4 (2009).
Lee et al., "Prioritizing candidate disease genes by network-based boosting of genome-wide association data," Genome Research, 21(1):1109-1121 (2011).

Lee et al., "The outcome and long-term follow-up of 94 patients with recurrent and refractory *Clostridium difficile* infection using single to multiple fecal microbiota transplantation vie retention enema," *European Journal Clinical Microbiology Infect Dis.*, 33:1425-1428 (2014).
Lee, "A Prospective Randomized Multi-Centre Trial of Fresh vs. Frozen-and-Thawed Human Biotherapy (Fecal Transplant) for Recurrent Clostridium difficile Infection," U.S. National Institutes of Health, Clinical Study No. NCT01398969, pp. 1-4, last updated Feb. 27, 2014, Web, May 20, 2014 <http://clinicaltrials.gov/ct2/show/NCT01398969>.
Leis et al., "Fecal microbiota transplantation: a 'How-To' guide for nurses," *Collegian*, 22:445-451 (2015).
Leslie et al., "Trehalose and Sucrose Protect Both Membranes and Proteins in Intact Bacteria during Drying," Applied and Environmental Microbiology, 61:3592-3597 (1995).
Lewis et al., "Stool form scale as a useful guide to intestinal transit time," *Scand. J Gastroenterol.*, 32(9):920-924 (1997).
Ley et al., "Ecological and evolutionary forces shaping microbial diversity in the human intestine," *Cell*, 124:837-848 (2006).
Ley et al., "Evolution of mammals and their gut microbes," *Science*, 320(5883): 1647-1651 (2008).
Ley et al., "Microbial ecology: human gut microbes associated with obesity," *Nature*, 444(7122):1022-3 (2006).
Ley et al., "Worlds within worlds: evolution of the vertebrate gut microbiota," *Nat. Rev. Microbial.*, 6(10):776-788 (2008).
Lin et al., "Twelve Week Storage Trial of Microbial Viability in Lyophilized and Frozen Fecal Microbiota Preparations," Poster Presentation—Digestive Disease Week 2015, Washington, D.C. USA.
Longstreth, "Irritable bowel syndrome: a multibillion-dollar problem," Gastroenterology,276. 109(6):2029-2031 (1995).
Loo et al., "A predominantly clonal multi institutional outbreak of Clostridium difficile-associated diarrhea with high morbidity and mortality," N Engl J Med, 353(23):2442-9 (2005).
Loo et al., "Host and pathogen factors for Clostridium difficile infection and colonization," N Engl J Med, 365(18):1693-703 (2011).
Louie et al., "Fidaxomicin versus vancomycin for Clostridium difficile infection," *N Engl. J. Med.*, 364(5):422-431 (2011).
Louie et al., "Home-based fecal flora infusion to arrest multiply-recurrent C. difficile infection," ICAAC/IDSA Conference, Abstract #K-4201 (2008).
Louis et al., "Diversity, metabolism and microbial ecology of butyrate-producing bacteria from the human large intestine," *FEMS Microbiology Letters*, 294:1-8 (2009).
Lu, "Taboo transplant: How new poo defeats superbugs," Science News, 1:90-91 (2011).
Ludwig et al., "Taxonomic outline of the *phylum Firmicutes*," Bergey's Manual of Systematic Bacteriology, 3:15-17 (2009).
Lund-Tonnesen et al., "Clostridium difficile-associated diarrhea treated with homologous faeces," *Tidsskr nor Lageforen*, 118:1027-1030 (1998).
MacConnachie et al., "Faecal transplant for recurrent Clostridium difficile-associated diarrhoea: a UK case series," *QJM*, 102(11):781-784 (2009).
MacDonald et al., "Formation of Ursodeoxycholic Acid from Chenodeoxycholic Acid by a 7b-Hydroxysteroid Dehydrogenase-Elaborating Eubacterium aerofaciens Strain Cocultured with 7a-Hydroxysteroid Dehydrogenase-Elaborating Organisms," Applied and Environmental Microbiology, 44(5):1187-1195 (1982).
Macpherson et al., "Induction of Protective IgA by Intestinal Dendritic Cells Carrying Commensal Bacteria," *Science*, 303:1662-1665 (2004).
Madsen, "The use of probiotics in gastrointestinal disease," Can J Gastroenterol, 15(12):817-22 (2001).
Maizels et al., "Regulatory T cells in Infection," *Advances in Immunology*, Chapter 3, 112:73-136 (2011).
Manichanh et al., "Reshaping the gut microbiome with bacterial transplantation and antibiotic intake," Genome Research 20:1411-1419 (2010).
Marchesi et al., "The normal intestinal microbiota," *Curr. Opin. Infect. Dis.*, 20(5):508-513 (2007).

(56) References Cited

OTHER PUBLICATIONS

Martin, "Development and Delivery of a Treatment for Clostridium difficile," *Bacteriotherapy*, pp. 1-2, n.d., Web, Feb. 10, 2012 <www.bacteriotherapy.org>.
Martin-Dejardin et al., "A way to follow the viability of encapsulated Bifidobacterium bifidum subjected to a freeze-drying process in order to target the colon: Interest of flow cytometry," European Journal of Pharmaceutical Sciences, 49:166-74 (2013).
Maslowski et al., "Diet, gut microbiota and immune responses," *Nat Immunol.*, 12(1):5-9 (2011).
McDonald et al., "An Epidemic, Toxin Gene-Variant Strain of Clostridium difficile," *N Engl J Med.*, 353(23):2433-41 (2005).
McDonald et al., "Clostridium difficile Infection in Patients Discharged from US Short-stay Hospitals, 1996-2003" *Emerg. Infect. Dis*, 12(3):409-415 (2006).
McFarland et al., "Breaking the Cycle: Treatment Strategies for 163 Cases of Recurrent Clostridium difficile Disease," *Am. J. Gastroenterol.*, 97(7):1769-1775 (2002).
McFarland et al., "Implications of the changing face of Clostridium difficile disease for health care practitioners," *Am J Infect Control.*, 35(4):237-253 (2007).
McFarland et al., "Meta-Analysis of Probiotics for the Prevention of Antibiotic Associated Diarrhea and the Treatment of Clostridium difficile Disease," *Am J Gastroenterol.*, 101(4):812-22 (2006).
McFarland et al., "Nosocomial Acquisition of Clostridium Difficile Infection," *N Engl J Med.*, 320(4):204-210 (1989).
McFarland et al., "Recurrent Clostridium Difficile Disease: Epidemiology and Clinical Characteristics," *Infect Control Hosp Epidemiol.*, 20(1):43-50 (1999).
McFarland et al., "Renewed interest in a difficult disease: Clostridium difficile infections—epidemiology and current treatment strategies," *Curr Opin Gastroenterol.*, 25(1):24-35 (2008).
Miller et al., "Health care-associated Clostridium difficile infection in Canada: patient age and infecting strain type are highly predictive of severe outcome and mortality," Clin Infect Dis., 50(2):194-201 (2010).
Miller et al., "Long-term follow-up of patients with fulminant Clostridium difficile colitis," *J Gastrointest. Surg.*, 13(5):956-959 (2009).
Miller et al., "Morbidity, mortality, and healthcare burden of nosocomial Clostridium difficile-associated diarrhea in Canadian hospitals," *Infect Control Hosp Epidemiol.*, 23(3):137-40 (2002).
Miller, "The fascination with probiotics for Clostridium difficile infection: lack of evidence for prophylactic or therapeutic efficacy," *Anaerobe*, 15(6):281-284 (2009).
Moayyedi et al., "Fecal Microbiota Transplantation Induces Remission in Patients With Active Ulcerative Colitis in a Randomized Controlled Trial," Gastroenterology, 149(1):102-9 (2015).
Molecular Studies in Autism, 2004 Funding Cycle, Cure Autism Now, Cure Autism Now Foundation, pp. 1-7 (2005) <www.cureautismnow.org>.
Momose et al., "16S rRNA gene sequence-based analysis of clostridia related to conversion of germfree mice to the normal state," *Journal of Applied Microbiology*, 107:2088-2097 (2009).
Morris et al., "Clostridium difficile Colitis: an Increasingly Aggressive Iatrogenic Disease?" *Arch Surg.*, 137(10):1096-1100 (2002).
Mucosal immunity: homeostasis (WS-064): Chairpersons: Toshiaki Ohteki, Makoto Iwata, *International Immunology*, 22:Suppl 1 Pt. 3, 1-9 (2010).
Mullard, "Microbiology: the Inside Story," *Nature*, 453:578-580 (2008).
Murai et al., "Interleukin 10 acts on regulatory T cells to maintain expression of the transcription factor Foxp3 and suppressive function in mice with colitis," *Nat Immunol.*, pp. 1-20 (2009).
Mutaflor, "Brief Summary of Therapeutic Principles," Ardeypharm GmbH 0796 D-58313 Herdecke Germany, 6 pgs (2006).
Mutaflor, "For Functional and Inflammatory Bowel Diseases for Extraintestinal Manifestations for Activation of the Body's In-Built Defences," Ardeypharm GmbH 0796, D-58313 Herdecke Germany, 8 pgs (2006).
Mutaflor, "Safety of Therapy," Ardeypharm GmbH 0796, D-58313 Herdecke Germany, 4 pgs (1988).
Muto et al., "A Large Outbreak of Clostridium difficile-Associated Disease with an Unexpected Proportion of Deaths and Colectomies at a Teaching Hospital Following Increased Fluoroquinolone Use," *Infect Control Hosp Epidemiol.*, 26(3):273-80 (2005).
Nieuwdorp et al., ["Treatment of recurrent Clostridium difficile-associated diarrhoea with a suspension of donor faeces"], *Ned Tijdschr Geneeskd*, 152(35):1927-32 (2008) (English abstract).
Niu et al., "Prevalence and Impact of Bacteriophages on the Presence of *Escherichia coli* O157:H7 in Feedlot Cattle and Their Environment," Applied and Environmental Microbiology, 75(5):1271-8 (2009).
O'Hara et al., "The gut flora as a forgotten organ," *EMBO Rep.*, 7(7):688-693 (2006).
O'Brien et al., "The emerging infectious challenge of clostridium difficile-associated disease in Massachusetts hospitals: clinical and economic consequences," Infect Control Hosp Epidemiol., 28(11):1219-27 (2007).
O'Connor et al., "Clostridium difficile Infection Caused by the Epidemic BI/NAP1/027 Strain," *Gastroenterology*, 136(6):1913-1924 (2009).
Office Action dated Sep. 18, 2015, in European Patent Application No. 11 728 077.6.
O'Garra et al., "IL-10-producing and naturally occurring CD4+ Tregs: limiting collateral damage," *The Journal of Clinical Investigation*, 114:1372-1378 (2004).
O'Hara et al., "Functional modulation of human intestinal epithelial cell responses by Bifidobacterium infantis and Lactobacillus salivarius," *Immunology* 118:202-215 (2006).
Okada et al., "Effects of Fecal Microorganisms and Their Chloroform-Resistant Variants Derived from Mice, Rats, and Humans on Immunological and Physiological Characteristics of the Intestines ofExgermnfree Mice," *Infection and Immunity*, 62(12):5442-5446 (1994).
Olson et al., "The Gut Microbiota Mediates the Anti-Seizure Effects of the Ketogenic Diet," Cell, 173:1728-1741 (2018) <https://linkinghub.elsevier.com/retrieve/pii/S0092867418305208>.
Ott et al., "Efficacy of Sterile Fecal Filtrate Transfer for Treating Patients With Clostridium difficile Infection," Gastroenterology, 152(4):799-811 (2017).
Paramsothy et al., "Gastroenterologist perceptions of faecal microbiota transplantation," *World J Gastroenterol*, 21(38): 10907-10914 (2015).
Paramsothy et al., "Multidonor intensive faecal microbiota transplantation for active ulcerative colitis: a randomised placebo-controlled trial," The Lancet, published online, 11 pages (2017).
Paterson et al., "Putting back the bugs: Bacterial treatment relieves chronic diarrhoea," *Med J Aus*, 160:232-233 (1994).
Patterson et al., "Special organism isolation: attempting to bridge the gap," *Infect Control Hosp Epidemiol.*, 15(5):335-338 (1994).
Pearce et al., "Modification of the colonic microflora using probiotics: the way forward?," *Gut*, 4l(Suppl 3):A63 (1997).
Pearce et al., "The use of probiotic therapy as a novel approach to the management of irritable bowel syndrome: a preliminary study," *J Gastroenterol & Hepatol*, 12(Suppl):A129 (1997).
Pepin et al., "Clostridium difficile-associated diarrhea in a region of Quebec from 1991 to 2003: a changing pattern of disease severity," *CMAJ*, 171(5):466-472 (2004).
Pepin et al., "Emergence of Fluoroquinolones as the Predominant Risk Factor for Clostridium difficile-Associated Diarrhea: a Cohort Study During an Epidemic in Quebec," *Clin Infect Dis.*, 41(9):1254-1260 (2005).
Pepin et al., "Management and Outcomes of a First Recurrence of Clostridium difficile-Associated Disease in Quebec, Canada," *Clin. Infect. Dis.*, 42:758-764 (2006).
Persky et al., "Treatment of recurrent Clostridium difficile-associated diarrhea by administration of donated stool directly through a colonoscope," *Am J Gastroenterol.*, 95(11):3283-3285 (2000).
Petrof et al., "Stool substitute transplant therapy for the eradication of Clostridium difficile infection: 'RePOOPulating' the gut," *Microbiome*, 1:3 (2013).
Petrof, "Harnessing the healthy gut microbiota to cure patients with recurrent C. difficile infection," U.S. National Institutes of Health,

(56) References Cited

OTHER PUBLICATIONS

Clinical Study No. NCT01372943, pp. 1-2, last updated Nov. 6, 2013, Web, May 22, 2014 <http://clinicaltrials.gov/ct2/show/NCT01372943>.
Pillai et al., "Probiotics for treatment of Clostridium difficile-associated colitis in adults (Review)," *Cochrane Database Syst Rev.*, (1):CD004611 (2008).
Porter, "Coating of pharmaceutical dosage forms," In D.B. Troy (Ed.), Remington: the Science and Practice of Pharmacy, Chapter 46, pp. 929-938 (2005).
Poster 064-03 presented at the 14th International Congress of Immunology, Aug. 22-27, 2010, in Kyoto (Atarashi et al., Regulation of colonic regulatory T cells by Clostridium species).
Prakash et al., "Colon-targeted delivery of live bacterial cell biotherapeutics including microencapsulated live bacterial cells," *Biologics: Targets & Therapy*, 2(3):355-378 (2008).
Prevention of Sudden Infant Death Syndrome, Healthtouch.com, Thomson Micromedex, pp. 1-4, n.d., Web, Nov. 23, 2005.
Qiu et al., "*Faecalibacterium prausnitzii* upregulates regulatory T cells and anti-inflammatory cytokines in treating TNBS-induced colitis," *Journal of Crohn's and Colitis*, 7:e558-e568 (2013).
Rabeneck et al., "Bleeding and perforation after outpatient colonoscopy and their risk factors in usual clinical practice," *Gastroenterology*, 135(6):1899-1906 (2008).
Rager et al., "Evaluation of rumen transfaunation after surgical correction of left-sided displacement of the abomasum in cows," *J Am. Vet. Med. Assoc.*, 225(6):915-920 (2004).
Ramesh et al., "Prevention of Clostridium difficile-induced ileocecitis with Bacteriophage," *Anaerobe*, 5:69-78 (1999).
Rao et al., "Evaluation of gastrointestinal transit in clinical practice: position paper of the American and European Neurogastroenterology and Motility Societies," *Neurogastroenterol. Motil.*, 23(1):8-23 (2011).
Rautava, "Potential uses of probiotics in the neonate," Seminars in Fetal & Neonatal Medicine, 12:45-53 (2007).
Rea et al., "Gut solutions to a gut problem: bacteriocins, probiotics and bacteriophage for control of Clostridium difficile infection," Journal of Medical Microbiology, 62:1369-1378 (2013).
Redelings et al., "Increase in Clostridium difficile-related mortality rates, United States, 1999-2004," *Emerg Infect Dis.*, 13(9):1417-1419 (2007).
Response to Office Action filed Feb. 25, 2014, in European Patent Application No. 11728077.6.
Response to Office Action filed Jan. 28, 2015, in European Patent Application No. 11728077.6.
Response to Office Action filed Nov. 18, 2015, in European Patent Application No. 11728077.6.
Rex et al., "American College of Gastroenterology guidelines for colorectal cancer screening 2008," *Am. J. Gastroenterol.*, 104(3):739-750 (2009).
Ricciardi et al., "Increasing prevalence and severity of Clostridium difficile colitis in hospitalized patients in the United States," *Arch Surg.*, 142(7):624-631 (2007).
Roberts, Generation and Development Microbial Drug Products, CSO Vedanta Biosciences, 1st Microbiome Drug Development Summit, pp. 1-17 (2016).
Rodemann et al., "Incidence of Clostridium difficile infection in inflammatory bowel disease," *Clin Gastroenterol Hepatol.*, 5(3):339-344 (2007).
Rohlke et al., "Fecal flora reconstitution for recurrent Clostridium difficile infection: results and methodology," *J Clin Gastroenterol.*, 44(8):567-570 (2010).
Rolfe et al., "Bacterial interference between Clostridium difficile and normal fecal flora," *J Infect Dis.*, 143(3):470-475 (1981).
Rossen et al., "Findings From a Randomized Controlled Trial of Fecal Transplantation for Patients with Ulcerative Colitis," Gastroenterology, 149(1):110-8 (2015).
Round et al., "Inducible Foxp3+ regulatory T-cell development by a commensal bacterium of the intestinal microbiota," *PNAS*, 107(27):12204-12209 (2010).
Round et al., "The gut microbiota shapes intestinal immune responses during health and disease," *Nat. Rev. Immunol.*, 9(5):313-323 (2009).
Rupnik et al., "Clostridium difficile infection: new developments in epidemiology and pathogenesis," *Nat. Rev. Microbial.*, 7(7):526-536 (2009).
Russell et al., "Fecal bacteriotherapy for relapsing Clostridium difficile infection in a child: a proposed treatment protocol," *Pediatrics*, 126(1):e239-42 (2010).
Sambol et al., "Colonization for the prevention of *Clostridium difficile* disease in hamsters," *J Infect. Dis.*, 186(12):1781-1789 (2002).
Sanchez et al., "The Role of Natural Regulatory T cells in Infection," *Immunol Res.*, 49(0):124-134 (2011).
Sandler et al., "Possible Gut-Brain Interaction Contributing to Delayed Onset Autism Symptomatology," Fourth Int. Symp. Brain-Gut Interactions, Blackwell Science Ltd., 10(4):33 (1998).
Sandler et al., "Short-Term Benefit From Oral Vancomycin Treatment of Regressive-Onset Autism," Journal of Child Neurology, 15(7):429-435 (2000).
Sartor, "Therapeutic correction of bacterial dysbiosis discovered by molecular techniques," *PNAS*, 105(43):16413-16414 (2008).
Schiller, "Review article, the therapy of constipation," Ailment Pharmacol. Ther., 15:749-763 (2001).
Schloss, "Introducing mothur: Open-Source, Platform-Independent, Community-Supported Software for Describing and Comparing Microbial Communities," *Appl. Environ. Microbial.*, 75(23):7537-7541 (2009).
Schwan et al., "Relapsing *Clostridium difficile* Enterocolitis Cured by Rectal Infusion of Homologous Faeces," *The Lancet*, 322(8354):845 (1983).
Schwan et al., "Relapsing *Clostridium difficile* Enterocolitis Cured by Rectal Infusion of Normal Faeces," *Scand. J Infect. Dis.*, 16(2):211-215 (1984).
Seeff et al., "How many endoscopies are performed for colorectal cancer screening? Results from CDC's survey of endoscopic capacity," *Gastroenterology*, 127:1670-1677 (2004).
Sekirov et al., "Gut microbiota in health and disease," *Physiol. Rev.*, 90(3):859-904 (2010).
Sell et al., "Bacteriophage and Bacteriocin Typing Scheme for Clostridium difficile," Journal of Clinical Microbiology, 17(6):1148-1152 (1983).
Setlow, "I Will Survive: Protecting and Repairing Spore DNA," Journal of Bacteriology, 174(9):2737-2741 (1992).
Setlow, "The bacterial spore: nature's survival package," Culture, 26(2):1-4 (2005).
Sghir et al., "Quantification of Bacterial Groups within Human Fecal Flora by Oligonucleotide Prode Hybridization," *Applied and Environmental Microbiology*, 66(5):2263-2266 (2000).
Shannon et al., "The Mathematical Theory of Communication," The University of Illinois Press, Urbana pp. 117 (1949).
Shi et al., "Fecal Microbiota Transplantation for Ulcerative Colitis: a Systematic Review and Meta-Analysis," PLoS One, 1-18 (2016).
Shim et al., "Primary symptomless colonisation by *Clostridium difficile* and decreased risk of subsequent diarrhea," *The Lancet*, 351(9103):633-666 (1998).
Silverman et al., "Success of self-administered home fecal transplantation for chronic Clostridium difficile infection," *Clin. Gastroenterol. Hepatol.*, 8(5):471-473 (2010).
Simor et al., "Clostridium difficile in long-term-care facilities for the elderly," *Infect Control Hosp Epidemiol.*, 23(11):696-703 (2002).
Singh et al., "Do NSAIDs, antibiotics, infections, or stress trigger flares in IBD?" *Am J Gastroenterol.*, 104(5):1298-1313 (2009).
Sleator, "The human superorganism—of microbes and men," *Med. Hypotheses*, 74(2):214-215 (2010).
Smits et al., "Therapeutic potential of fecal microbiota transplantation," Gastroenterology, 145:946-953 (2013).
Sokol et al., *Faecalibacterium prausnitzii* is an anti-inflammatory commensal bacterium identified by gut microbiota analysis of Crohn disease patients, *Proceedings of the National Academy of Sciences*, 105(43):16731-16736(2008).
Sokol et al., "Low Counts of *Faecalibacterium prausnitzii* in Colitis Microbiota," *Injlamm. Bowel Dis.*, pp. 1-7 (2009).

(56) References Cited

OTHER PUBLICATIONS

Sullivan et al., "Effect of supplement with lactic-acid producing bacteria on fatigue and physical activity inpatients with chronic fatigue syndrome," Nutritional Journal, 8(4):1-6 (2009).
Sunil et al., "Design and evaluation of lomoxicam bilayered tablets for biphasic release," Brazilian Journal of Pharmaceutical Sciences, 48(4):609-19 (2012).
Surawicz et al., "Treatment of refractory and recurrent Clostridium difficile infection," *Nat. Rev. Gastroenterol. Hepatol.*, 8(6):330-339 (2011).
Surawicz, "Reining in Recurrent Clostridium difficile Infection—Who's at Risk?," *Gastroenterology*, 136:1152-1154 (2009).
Sutherland et al., "Lyophilized Clostridium perfringens 3 alpha- and Clostridium bifermentans 7 alpha-hydroxysteroid dehydrogenases: two new stable enzyme preparations for routine bile acid analysis," Biochim Biophys Acta, 962(1):116-121 (1988).
Takaishi et al., "Imbalance in intestinal microflora constitution could be involved in the pathogenesis of inflammatory bowel disease," *J. Med. Microbial.*, 298:463-472 (2008).
Takeda et al., "Serum Haloperidol Levels of Schizophrenics Receiving Treatment for Tuberculosis," Clinical Neuropharmacology, 9(4):386-397 (1986).
Tan et al., "Predictors of acute diverticulitis severity: a systematic review," *International Journal of Surgery* 26:43-52 (2016).
Tannock et al., "A new macrocyclic antibiotic, fidaxomicin (OPT-80), causes less alteration to the bowel microbiota of Clostridium difficile-infected patients than does vancomycin," *Microbiology*, 156(11):3354-3359 (2010).
Tanoue et al., "Immune response to gut microbiota-commensals and pathogens," Gut Microbes, 1(4):224-233 (2010).
Taras et al., "Reclassification of Eubacterium formicigenerans Holdeman and Moore 1974 as *Dorea formicigenerans* gen. nov., comb. nov., and description of *Dorea longicatena* sp. nov., isolated from human faeces," *International Journal of Systematic and Evolutionary Microbiology*, 52:423-428 (2002).
Teasley et al., "Prospective randomised trial of metronidazole versus vancomycin for Clostridium-difficile-associated diarrhoea and colitis," *The Lancet*, 2(8358):1043-1046 (1983).
Tian et al., "Freeze-dried, Capsulized Fecal Microbiota Transplanation for Relapsing Clostridium difficile Infection," Journal of Clinical Gastroenterology, 49(6):537-538 (2015).
Tilg et al., "Gut microbiome, obesity, and metabolic dysfunction," *J Clin. Invest.*, 121(6):2126-2132 (2011).
Tursi et al., "Preventing recurrent acute diverticulitis with pharmacological therapies," *Ther Ad Chronic Dis* 4(6)277-286 (2013).
Tursi et al., "Randomised clinical trial: mesalazine and/or probiotics in maintaining remission of symptomatic uncomplicated diverticular disease—a double-blind, randomized, placebo-controlled study," *Alimentary Pharmacology and Therapeutics* 38:741-751 (2013).
Tvede et al., "Bacteriotherapy for chronic relapsing Clostridium difficile diarrhea in six patients," *The Lancet*, 1:1156-1160 (1989).
Van Andel et al., "Interleukin-12 Has a Role in Mediating Resistance of Murine Strains to Tyzzer's Disease," Infect. Immun., 66(10):4942-4946 (1998).
Van der Waaij et al., "Direct Flow Cytometry of Anaerobic Bacteria in Human Feces," *Cytometry*, 16:270-279 (1994).
Van Immerseel et al., "Butyric acid-producing anaerobic bacteria as a novel probiotic treatment approach for inflammatory bowel disease," *Journal of Medical Microbiology*, 59:141-143 (2010).
Van Nood et al., "Struggling with Recurrent Clostridium difficile Infections: Is Donor Faeces the Solution?," *Euro Surveill.*, 14(34):1-6 (2009).
Van Nood, "Duodenal infusion of donor feces for recurrent Clostridium difficile," *New England Journal of Medicine*, 368(5):407-415 (2013).
Vaughn et al., "Novel treatment options for ulcerative colitis," *Future Science*, 1-20 (2013).
Veldhuyzen van Zanten et al., "Drug Treatment of Functional Dyspepsia: a Systematic Analysis of Trial Methodology with Recommendations for Design of Future Trials," *Am. J Gastroenterol.*, 91(4):660-673 (1996).
Veldhuyzen van Zanten et al., "Validation of a 7-point Global Overall Symptom scale to measure the severity of dyspepsia symptoms in clinical trials," *Ailment Pharmacol. Ther.*, 23(4):521-529 (2006).
Venugopal et al., "Fidaxomicin: a Novel Macrocyclic Antibiotic Approved for Treatment of Clostridium difficile Infection," *Clin Infect Dis*, 54(4):568-74 (2012).
Vrieze et al., "The environment within: how gut microbiota may influence metabolism and body composition," *Diabetologia*, 53(4):606-613 (2010).
Vulevic et al., "Modulation of the fecal microflora profile and immune function by a novel trans-galactooligosaccharide mixture (B-GOS) in healthy elderly volunteers," Am J Clin Nutr, 88:1438-46 (2008).
Wachsmann et al., "Characterization of an Orotic Acid Fermenting Bacterium, *Zymobacterium oroticum*, nov. gen., nov. spec.," *Journal of Bacteriology*, 68(4):400-404 (1954).
Walter et al., "Host-microbial symbiosis in the vertebrate gastrointestinal tract and the Lactobacillus reuteri paradigm," *PNAS USA*, 108(Suppl 1):4645-4652 (2011).
Warny et al., "Toxin production by an emerging strain of Clostridium difficile associated with outbreaks of severe disease in North America and Europe," Lancet, 366(9491):1079-84 (2005).
Warren et al., "*Clostridium aldenense* sp. nov. and *Clostridium citroniae* sp. nov. Isolated from Human Clinical Infections," *Journal of Clinical Microbiology*, 44(7):2416-2422 (2006).
Wasfy et al., "Comparison of Preservation Media for Storage of Stool Samples," Journal of Clinical Microbiology, 33(8):2176-2178 (1995).
Weingarden et al., "Dynamic changes in short- and long-term bacterial composition following fecal microbiota transplantation for recurrent Clostridium difficile infection," Microbiome, 3(10), 8 pages (2015).
Weissman et al., "Stool Transplants: Ready for Prime Time?," Current Gastroenterology Reports, 14:313-316 (2012).
Wells et al., "Clostridia: Sporeforming Anaerobic Bacilli," *Medical Microbiology-NCBI Bookshelf*, 4th Edition, Chapter 18, pp. 1-20 (1996) <https://www.ncbi.nlm.nih.gov/books/NBK8219/?report=printable>.
Wenisch et al., "Comparison of Vancomycin, Teicoplanin, Metronidazole, and Fusidic Acid for the Treatment of Clostridium difficile-Associated Diarrhea," *Clin Infect Dis.*, 22(5):813-818 (1996).
Wettstein et al., "Fecal Bacteriotherapy—an effective Treatment for Relapsing Symptomatic Clostridium difficile Infection," Abstract, 15th United European Gastroenterology Week (UEGW) Poster presentations, United European Gastroenterology Federation, France, A303 (2007).
Wettstein et al., "Skewered diverticulum: another cause of abdominal pain," *Internal MedJ*, 31(8):495-496 (2001).
Wikoff et al., "Metabolomics analysis reveals large effects of gut microflora on mammalian blood metabolites," *PNAS*, 106(10):3698-3703 (2009).
Wilson et al., "Human Colonic Biota Studied by Ribosomal DNA Sequence Analysis," *Appl. Environ. Microbial.*, 62(7):2273-2278 (1996).
Yoon et al., "Treatment of Refractory/Recurrent C. difficile-associated Disease by Donated Stool Transplanted Via Colonoscopy: a Case Series of 12 patients," *J Clin Gastroenterol.*, 44(8):562-566 (2010).
You et al., "Successful treatment of fulminant Clostridium difficile infection with fecal bacteriotherapy," *Ann. Intern. Med.*, 148(8):632-633 (2008).
Youngster et al., "Oral, Capsulized, Frozen Microbiota Transplantation for Relapsing Clostridium difficile Infection," *American Medical Association*, 312 (174) 1772-1778 (2014).
Yue et al., "Similarity Measure Based on Species Proportions," *Commun. Stat. Theor. Methods*, 34(11):2123-2131 (2005).
Zar et al., "A Comparison of Vancomycin and Metronidazole for the Treatment of Clostridium difficile-Associated Diarrhea, Stratified by Disease Severity," *Clin Infect Dis.*, 45(3):302-307 (2007).
Zhang et al, "Influence of Microbiota on Intestinal Immune System in Ulcerative Colitis and Its Intervention," Frontiers in Immunology, 8(Article 1674):1-11 (2017).

(56) References Cited

OTHER PUBLICATIONS

Zhang et al., "Altered gut microbiome composition in children with refractory epilepsy after ketogenic diet," *Epilepsy Research* (2018) <https://doi.org/10.1016/j.eplepsyres.2018.06.15>.

Zhou et al., "Total fecal microbiota transplantation alleviates high-fat diet-induced steatohepatitis in mice via beneficial regulation of gut microbiota," *Scientific Reports* (*Nature*), 7(1529):1-11 (2017).

Zilberberg et al., "Clostridium difficile Infections amoung Hospitalized Children," Emerg. Infect. Dis, 16(4):604-609 (2010).

Zilberberg et al., "Clostridium difficile-related Hospitalizations amoung US Adults," Emerg. Infect. Dis, 15(1):122-124 (2009).

Zilberberg et al., "Increase in Adult Clostridium difficile-related Hospitalization and Case-Fatality Rate," Emerg. Infect. Dis, 14(6):929-931 (2008).

Zilberberg et al., "Increase in Clostridium difficile-related Hospitalizations Among Infants in the United States, 2001-2005" Pediatr Infect Dis. J, 27(12):1111-1113 (2008).

Zoppi et al., "Oral Bacteriotherapy in Clinical Practice," Eur J. Pediatr, 139(1):18-21 (1982).

Zoppi et al., "The Intenstinal Ecosystem in Chronic Functional Constipation," ACTA Paediatr, 836-841 (1998).

\* cited by examiner

COMPOSITIONS AND METHODS FOR TREATING DIVERTICULITIS AND RELATED DISORDERS

CROSS-REFERENCE TO RELATED APPLICATIONS

This application claims priority to U.S. Provisional Application No. 62/482,159, filed Apr. 5, 2017. The U.S. Provisional Application is incorporated by reference herein in its entirety.

FIELD

The present disclosure relates to pharmaceutical compositions and methods suitable for treating gastrointestinal (GI) disorders, such as recurrent diverticulitis.

BACKGROUND

Mammals harbor diverse microbial species in their gastrointestinal (GI) tracts. Interactions between these microbes and between microbes and the host, e.g. the host immune system, shape a microbiota. A healthy microbiota provides the host with multiple benefits, including colonization resistance to a broad spectrum of pathogens, essential nutrient biosynthesis and absorption, and immune stimulation that maintains a healthy gut epithelium and an appropriately controlled systemic immunity. An unbalanced microbiota (also called 'dysbiosis' or disrupted symbiosis) may lose its function and result in increased susceptibility to pathogens, altered metabolic profiles, or induction of proinflammatory signals that can lead to local or systemic inflammation or autoimmunity. Additionally, such a disrupted microbiota may be infected by incoming pathogen or pathogens, which can cause pain, diarrhea, gas, constipation among other symptoms. Hence. the intestinal microbiota plays a significant role in the pathogenesis of many disorders such as pathogenic infections of the gut.

Implantation or administration of human colonic microbiota into the bowel of a sick patient is called Fecal Microbiota Transplantation (FMT), also commonly known as fecal bacteriotherapy. FMT is believed to repopulate the gut with a diverse array of microbes that control key pathogens by creating an ecological environment inimical to their proliferation and survival. It represents a therapeutic protocol that allows a fast reconstitution of a normal compositional and functional gut microbial community.

FMT has been used to treat *Clostridium difficile* infection (CDI). FMT has also been suggested in treating other gut infective agents such as *E. coli* and Vancomycin resistant Enterococci (VRE). It entails infusions through a colonoscope, an enema or via a nasojejunal tube of human microbiota either in the form of homogenised stool, or cultured stool components such as Clostridia, to implant in the colon and thereby displace or eradicate pathogenic bacteria, e.g., *C. difficile*.

Diverticular disease includes a spectrum of conditions ranging from asymptomatic diverticular disease, to symptomatic uncomplicated diverticular disease, and complicated diverticular disease that includes acute and chronic diverticulitis. Diverticulitis is defined as an inflammation of one or more diverticula, which are small pouches created by herniation of the mucosa into the wall of the colon. Diverticulitis patients typically present with symptoms of pain of the lower left quadrant, fever, nausea and vomiting, or abnormal bowel habits (constipation or diarrhea). Complicated diverticulitis may also be associated abscess, phlegmon, fistula, stricture, stenosis, obstruction, bleeding, or perforation.

Diverticulitis is generally considered a disease of the elderly, but as many as 20% of patients with diverticulitis are younger than 50 years. Diverticulitis becomes more common after the age of 40, with risk continuing to increase with age. Certain drugs such as ibuprofen, naproxen, steroids, and opiates can increase diverticulitis risk. In its chronic form, patients may have recurrent bouts of low-grade or overt diverticulitis. In the United States, there are more than 200,000 cases of Diverticulitis per year.

More information on diverticulosis and diverticulitis can be found in the following references: Klarenbeek et al., *Int J Colorectal Dis* (2012) 27:207-14; Tursi, *Ther Adv Chronic Dis*. (2013) 4(6): 277-86; Tursi et al., *Aliment Pharmacol Ther* (2013) 38: 741-751; Andeweg et al., *Dig Surg* (2013) 30:278-92; Tan et al., *International Journal of Surgery* (2016) 26:43-52.

Current attempts for treating relapsing diverticulitis can range from maintaining a high-fiber diet, rest and antibiotics, for mild cases to surgery for severe and recurring (relapsing) diverticulitis. There is a need for more effective treatments for recurrent diverticulitis that are easier to administer.

SUMMARY

The present disclosure provides compositions, methods, and dosing regimens for treating or preventing recurrent diverticulitis.

In one aspect, the present disclosure provides a method for treating recurrent diverticulitis in a subject in need thereof, where the method comprises administering to the subject a pharmaceutically active dose of a therapeutic composition comprising or derived from live non-pathogenic fecal bacteria or a sterile fecal filtrate. In one aspect, a sterile fecal filtrate originates from a donor stool. In another aspect, a sterile fecal filtrate originates from cultured microorganisms.

In another aspect, this disclosure provides use of a composition comprising live non-pathogenic fecal bacteria in the manufacture of a medication for the treatment of recurrent diverticulitis.

In one aspect, the present disclosure provides a method for treating recurrent diverticulitis in a subject in need thereof, where the method comprises administering orally to the subject a pharmaceutically active dose of a therapeutic composition comprising live, non-pathogenic, synthetic bacterial mixture or live, non-pathogenic, purified or extracted, fecal microbiota, where the dose is administered at a dosing schedule of at least once or twice daily or at least once or twice weekly for at least three, eight, ten, or twenty consecutive weeks.

In one aspect, the present disclosure provides a method for treating recurrent diverticulitis in a subject in need thereof, where the method comprises administering orally to the subject a pharmaceutically active dose of a therapeutic composition comprising a liquid, frozen, lyophilized, or encapsulated sterile fecal filtrate, where the dose is administered at a dosing schedule of at least once or twice daily or at least once or twice weekly for at least three, eight, ten, or twenty consecutive weeks.

In one aspect, a method achieves a remission, cure, response, or resolution rate of recurrent diverticulitis of at least about 80%.

In an aspect, a fecal microbiota in a therapeutic composition comprises a donor's substantially entire and non-selected fecal microbiota, reconstituted fecal material, synthetic fecal material.

DETAILED DESCRIPTION

Unless defined otherwise herein, terms are to be understood according to conventional usage by those of ordinary skill in the relevant art.

As used herein, the term "treating" refers to (i) completely or partially inhibiting a disease, disorder or condition, for example, arresting its development; (ii) completely or partially relieving a disease, disorder or condition, for example, causing regression of the disease, disorder and/or condition; or (iii) completely or partially preventing a disease, disorder or condition from occurring in a patient that may be predisposed to the disease, disorder and/or condition, but has not yet been diagnosed as having it. Similarly, "treatment" refers to both therapeutic treatment and prophylactic or preventative measures.

As used herein, "therapeutically effective amount" or "pharmaceutically active dose" refers to an amount of a composition which is effective in treating the named disease, disorder or condition.

As used herein, "microbiota," and "flora" refer to a community of microbes that live in or on a subject's body, both sustainably and transiently, including eukaryotes, archaea, bacteria, and viruses (including bacterial viruses (i.e., phage)). A non-selected fecal microbiota refers to a community or mixture of fecal microbes derived from a donor's fecal sample without selection and substantially resembling microbial constituents and population structure found in such fecal sample.

As used herein, a "sterile fecal filtrate" or a "non-cellular fecal filtrate" refers to a liquid component of a fecal material, where the liquid component is free or substantially free of cell-based living organisms (e.g., bacteria, fungi, or their spores), but retains bacteriophages and non-cellular biological materials. Preferably, a non-cellular or sterile fecal filtrate is also free of viruses for eukaryotic host cells.

As used herein, "remission, cure, or resolution rate" refers to the percentage of patients that are cured or obtain remission or complete resolution of a condition in response to a given treatment. Remission, cure, or resolution of recurrent diverticulitis refers to complete cessation of one or more symptoms that a patient manifests prior to receiving a treatment described here. Such symptoms can include, but are not limited to left lower quadrant pain, abnormal bowel habits, nausea, vomiting, constipation, diarrhea, flatulence, bloating, abscess, phlegmon, fistula, stricture, stenosis, obstruction, bleeding, and perforation. Remission, cure, or resolution can be further confirmed by endoscopic and mucosal healing.

As used herein, "response rate" refers to the percentage of patients that respond positively (e.g., reduced severity or frequency of one or more symptoms) to a given treatment.

As used herein, "eukaryotic" refers to belonging to a cell that contains a nucleus and membrane-bound organelles.

As used herein, "bacteria," "bacterium," and "archaea" refer to single-celled prokaryotes that lack membrane bound nuclei and lack organelles.

As used herein, "colony forming units" (cfu) refers to an estimate of the number of viable microorganism cells in a given sample.

As used herein, "viable" means possessing the ability to multiply.

As used herein, "fecal bacteria" refers to bacteria that can be found in fecal matter.

As used herein, "isolated" or "purified" refers to a bacterium or other entity or substance that has been (1) separated from at least some of the components with which it was associated when initially produced (whether in nature or in an experimental setting), and/or (2) produced, prepared, purified, and/or manufactured by the hand of man. Isolated or purified bacteria can be separated from at least about 10%, about 20%, about 30%, about 40%, about 50%, about 60%, about 70%, about 80%, about 90%, or more of the other components with which they were initially associated.

As used herein, "cytotoxic" activity or bacterium includes the ability to kill a bacterial cell, such as a pathogenic bacterial cell. A "cytostatic" activity or bacterium includes the ability to inhibit, partially or fully, growth, metabolism, and/or proliferation of a bacterial cell, such as a pathogenic bacterial cell.

As used herein, the terms "pathogen" and "pathogenic" in reference to a bacterium or any other organism or entity includes any such organism or entity that is capable of causing or affecting a disease, disorder or condition of a host organism containing the organism or entity.

As used herein, "spore" or a population of "spores" includes bacteria (or other single-celled organisms) that are generally viable, more resistant to environmental influences such as heat and bacteriocidal agents than vegetative forms of the same bacteria, and typically capable of germination and out-growth. "Spore-formers" or bacteria "capable of forming spores" are those bacteria containing the genes and other necessary abilities to produce spores under suitable environmental conditions.

As used herein, a "combination" of two or more bacteria includes the physical co-existence of the two bacteria, either in the same material or product or in physically connected products, as well as the temporal co-administration or co-localization of the two bacteria.

As used herein, "subject" refers to any animal subject including humans, laboratory animals (e.g., primates, rats, mice), livestock (e.g., cows, sheep, goats, pigs, turkeys, chickens), and household pets (e.g., dogs, cats, rodents, etc.). The subject or patient may be healthy, or may be suffering from an infection due to a gastrointestinal pathogen or may be at risk of developing or transmitting to others an infection due to a gastrointestinal pathogen.

As used herein, "Shannon Diversity Index" refers to a diversity index that accounts for abundance and evenness of species present in a given community using the formula $$H = -\sum_{i=1}^{R} p_i \ln p_i$$

where H is Shannon Diversity Index, R is the total number of species in the community, and $p_i$ is the proportion of R made up of the ith species. Higher values indicate diverse and equally distributed communities, and a value of 0 indicates only one species is present in a given community. For further reference, see Shannon and Weaver, (1949) *The mathematical theory of communication*. The University of Illinois Press, Urbana. 117 pp.

As used herein, "antibiotic" refers to a substance that is used to treat and/or prevent bacterial infection by killing bacteria, inhibiting the growth of bacteria, or reducing the viability of bacteria.

As used herein, an "intermittent dosing schedule" means that that a therapeutic composition is administered for a period of time followed by a period of time (a treatment period) where treatment with such therapeutic composition is withheld (a rest period). Intermittent dosing regimens can be expressed as treatment period in days or weeks/rest period in days or weeks. For example, a 4/1 intermittent dosing schedule refers to an intermittent dosing schedule where the treatment period is four weeks/days and the rest period is one week/day.

As used herein, a "continuous dosing schedule" refers to a dosing schedule where a therapeutic composition is administered during a treatment period without a rest period. Throughout the treatment period of a continuous dosing schedule, a therapeutic composition can be administered, for example, weekly, daily, or every other day, or every third day. On a day when a therapeutic composition is administered, it can be administered in a single dose, or in multiple doses throughout the day.

As used herein, "dosing frequency" refers to the frequency of administering doses of a therapeutic composition in a given time. Dosing frequency can be indicated as the number of doses per a given time, for example, once per day, once a week, or once in two weeks.

As used herein, "dosing interval" refers to the amount of time that elapses between multiple doses being administered to a subject.

Diverticula are small mucosal herniations protruding through the intestinal layers and the smooth muscle along the natural openings created by the vasa recta or nutrient vessels in the wall of the colon. True diverticulae contain all layers of the gastrointestinal wall (mucosa, muscularis propria, and adventitia) (e.g., Meckel diverticulum). False diverticulae, or pseudo-diverticulae do not contain the muscular layers or adventitia, and they only involve the submucosa and mucosa. Diverticula can occur anywhere in the gastrointestinal tract but are usually observed in the colon. The sigmoid colon has the highest intraluminal pressures and is most commonly affected.

Diverticulae found in the left colon (predominantly in the sigmoid) are usually false diverticula, and they are commonly found in Western populations. Right-sided and cecal diverticulae, however, are more commonly true diverticulae, and they are usually found in people of Asian descent. Cecal diverticulae are generally rare compared to those found in the left colon.

Diverticulosis is defined as the condition of having uninflamed diverticula; it occurs commonly with increasing age. The cause of diverticulosis is not yet conclusive, but it appears to be associated with a low-fiber diet, constipation, and obesity.

Diverticulitis is defined as an inflammation of one or more diverticula. Its pathogenesis remains unclear. Fecal material or undigested food particles may collect in a diverticulum, causing obstruction. This obstruction may result in distension of the diverticula secondary to mucous secretion and overgrowth of normal colonic bacteria. Vascular compromise and subsequent microperforation or macroperforation then ensue. Alternatively, some believe that increased intraluminal pressure or inspissated food particles cause erosion of the diverticular wall, resulting in inflammation, focal necrosis, and perforation. The disease is frequently mild when pericolic fat and mesentery wall off a small perforation. However, larger perforations and more extensive disease lead to abscess formation and, rarely, intestinal rupture or peritonitis.

Fistula formation is a complication of diverticulitis. Fistulas to adjacent organs and the skin may develop, especially in the presence of an abscess. In men, colovesicular fistulas are the most common. In women, the uterus is interposed between the colon and the bladder, and this complication is only seen following a hysterectomy. The uterus precludes fistula formation from the sigmoid colon to the urinary bladder. However, colovaginal and colocutaneous fistulas can form but are uncommon.

Recurrent attacks of diverticulitis can result in the formation of scar tissue, leading to narrowing and obstruction of the colonic lumen. As used herein, recurrent diverticulitis, relapsing diverticulitits, or chronic diverticulitits are used interchangeably.

Many chronic diseases and disorders of the GI tract have chronic infection/infestation as their underlying pathological conditions (e.g., recurrent diverticulitis). In one aspect, the present disclosure includes and relates to the use of a fecal microbiota, one or more microbial species therefrom, an active fragment or component therefrom for the treatment and/or prophylaxis of various disease states (e.g., recurrent diverticulitis) related to the presence of 'abnormal' microflora in the GI tract. An active fragment of a bacterium can be any active molecule isolated from such bacteria by any known method for preparing/identifying active fragments of bacteria and proteins secreted from bacteria. Such methods include but are not limited to the following: sonication, osmotic shock, detergent lysis, high pressure, transfer appropriate DNA to other organisms, such as bacteria, plant or animal that is then used as a feed additive as described previously. In one aspect, an active fragment or component of a bacterium is selected from the group consisting of a mycolate or a derivative thereof, a polysaccharide, a lipoglycan, a small peptide, a thiopeptide, a protein, a nucleic acid molecule, a metabolite, a cell wall component, or any combination thereof. In one aspect, an active fragment is a protein or a secretion. In another aspect, an active fragment is a secreted protein.

In one aspect, the present disclosure provides a method for treating recurrent diverticulitis in a subject in need thereof, where the method comprises administering to the subject a pharmaceutically active dose of a therapeutic composition comprising live non-pathogenic fecal bacteria. In another aspect, this disclosure provides use of a composition comprising live non-pathogenic fecal bacteria in the manufacture of a medication for the treatment of recurrent diverticulitis.

In one aspect, a method provided here is for treating a form of diverticulitis selected from the group consisting of acute diverticulitis and recurrent diverticulitis. In one aspect, a therapeutic composition comprises an isolated or purified population of live non-pathogenic fecal bacteria. In one aspect, a therapeutic composition comprises a non-selected fecal microbiota. In another aspect, a therapeutic composition comprises a non-selected and substantially complete fecal microbiota. In another aspect, a therapeutic composition comprises a full-spectrum fecal microbiota. In one aspect, a method further comprises administering a 5-aminosalicylic acid agent, a corticosteroid, an immunosuppressant, or a combination thereof. In another aspect, a method further comprises administering 5-aminosalicylic acid or a derivative thereof, sulfasalazine or a derivative thereof, or a combination thereof.

In one aspect, the present disclosure provides a method which eliminates or reduces one or more recurrent diverticulitis symptoms selected from the group consisting of left lower quadrant pain, change in bowel habits, nausea, vomiting, constipation, diarrhea, flatulence, and bloating. In another aspect, the present disclosure provides a method which eliminates, improves, relieves, or reduces one or more recurrent diverticulitis symptoms selected from the group consisting of abscess, phlegmon, fistula, stricture, stenosis, obstruction, bleeding, and perforation.

In one aspect, a patient treated here stays on a high fiber diet. In another aspect, a patient treated here does not need to maintain a high fiber diet. In a further aspect, a patient treated here can achieve a cure without a high fiber diet. In one aspect, a patient treated here stays on an anti-inflammatory agent or drug. In another aspect, a patient treated here is capable of discontinuing an anti-inflammatory agent or drug. In a further aspect, a patient treated here achieves a remission or cure free of using any anti-inflammatory agent or drug.

In one aspect, a patient treated here stays on a clear liquid diet for at least 1, 2, 3, 4, 5, 6, or 7 days. In another aspect, a patient treated here does not need to undergo a clear liquid diet. In a further aspect, a patient treated here can achieve a cure without a clear liquid diet.

In one aspect, a patient treated here is pretreated with 7-10 days of oral broad-spectrum antimicrobial therapy. In one aspect, a single-agent antibiotic regimen is used. In another aspect, a multiple-agent antibiotic regimen is used. Exemplary antibiotic regimens include the following: (a) ciprofloxacin and metronidazole; (b) trimethoprim-sulfamethoxazole and metronidazole; (c) moxifloxacin, (d) amoxicillin/clavulanic acid. Further exemplary antibiotics include piperacillin/tazobactam, ampicillin/sulbactam, ticarcillin/clavulanic acid, imipenem, meropenem, tigecycline (when severe penicillin allergy is a concern). In another aspect, a multiple-drug regimen may consist of metronidazole and a third-generation cephalosporin or a fluoroquinolone, such as the following: Ceftriaxone, Cefotaxime, Ciprofloxacin, and Levofloxacin.

In one aspect, a patient subject to a treatment method described here comprises one or more surgical indications selected from the group consisting of free-air perforation with fecal peritonitis, suppurative peritonitis secondary to a ruptured abscess, uncontrolled sepsis, abdominal or pelvic abscess, fistula formation, inability to rule out carcinoma, and intestinal obstruction.

In one aspect, a patient subject to a treatment method described here does not exhibit one or more surgical indications selected from the group consisting of free-air perforation with fecal peritonitis, suppurative peritonitis secondary to a ruptured abscess, uncontrolled sepsis, abdominal or pelvic abscess, fistula formation, inability to rule out carcinoma, and intestinal obstruction.

In one aspect, the present disclosure provides a method for treating recurrent diverticulitis in a subject in need thereof, where the method comprises administering to the subject a pharmaceutically active dose of a therapeutic composition comprising live non-pathogenic bacteria. In one aspect, the present disclosure provides a method for treating recurrent diverticulitis in a subject in need thereof, where the method comprises administering daily or weekly to the subject a pharmaceutically active dose of a therapeutic composition comprising live non-pathogenic fecal bacteria. In one aspect, a therapeutic composition is administered to an recurrent diverticulitis patient in need thereof at least once daily or at least once weekly for at least two consecutive days or weeks. In one aspect, a therapeutic composition is administered at least once daily or at least once weekly for at least 3, 4, 5, 6, 7, 8, 9, 10, 11, 12, 13, 14, or 15 consecutive days or weeks. In another aspect, a therapeutic composition is administered at least once daily or at least once weekly for at least 1, 2, 3, 4, 5, 6, 7, 8, 9, 10, 11, or 12 consecutive weeks. In one aspect, a therapeutic composition is administered at least once daily or at least once weekly for at most 4, 5, 6, 7, 8, 9, 10, 11, 12, 13, 14, 15, 16, 17, 18, 19, or 20 consecutive days or weeks. In another aspect, a therapeutic composition is administered at least once daily or at least once weekly for at most 1, 2, 3, 4, 5, 6, 7, 8, 9, 10, 11, or 12 consecutive weeks or months. In a further aspect, a therapeutic composition is administered at least once for at least 1, 2, 3, 4, 5, 6, 7, 8, 9, 10, 11, or 12 consecutive months or years, chronically for a subject's entire life span, or an indefinite period of time.

In one aspect, a therapeutic composition is administered to an recurrent diverticulitis patient in need thereof at least twice daily or at least twice weekly for at least two consecutive days or weeks. In one aspect, a therapeutic composition is administered at least twice daily or at least twice weekly for at least 3, 4, 5, 6, 7, 8, 9, 10, 11, 12, 13, 14, or 15 consecutive days or weeks. In another aspect, a therapeutic composition is administered at least twice daily or at least twice weekly for at least 1, 2, 3, 4, 5, 6, 7, 8, 9, 10, 11, or 12 consecutive weeks. In one aspect, a therapeutic composition is administered at least twice daily or at least twice weekly for at most 4, 5, 6, 7, 8, 9, 10, 11, 12, 13, 14, 15, 16, 17, 18, 19, or 20 consecutive days or weeks. In another aspect, a therapeutic composition is administered at least twice daily or at least twice weekly for at most 1, 2, 3, 4, 5, 6, 7, 8, 9, 10, 11, or 12 consecutive weeks or months. In a further aspect, a therapeutic composition is administered at least twice for at least 1, 2, 3, 4, 5, 6, 7, 8, 9, 10, 11, or 12 consecutive months or years, chronically for a subject's entire life span, or an indefinite period of time.

In one aspect, a therapeutic composition is administered to an recurrent diverticulitis patient in need thereof at least three times daily or at least three times weekly for at least two consecutive days or weeks. In one aspect, a therapeutic composition is administered at least three times daily or at least three times weekly for at least 3, 4, 5, 6, 7, 8, 9, 10, 11, 12, 13, 14, or 15 consecutive days or weeks. In another aspect, a therapeutic composition is administered at least three times daily or at least three times weekly for at least 1, 2, 3, 4, 5, 6, 7, 8, 9, 10, 11, or 12 consecutive weeks. In one aspect, a therapeutic composition is administered at least three times daily or at least three times weekly for at most 4, 5, 6, 7, 8, 9, 10, 11, 12, 13, 14, 15, 16, 17, 18, 19, or 20 consecutive days or weeks. In another aspect, a therapeutic composition is administered at least three times daily or at least three times weekly for at most 1, 2, 3, 4, 5, 6, 7, 8, 9, 10, 11, or 12 consecutive weeks or months. In a further aspect, a therapeutic composition is administered at least three times for at least 1, 2, 3, 4, 5, 6, 7, 8, 9, 10, 11, or 12 consecutive months or years, chronically for a subject's entire life span, or an indefinite period of time.

In one aspect, the present disclosure provides a method for treating recurrent diverticulitis in a subject in need thereof, where the method comprises administering orally to the subject a pharmaceutically active dose of a therapeutic composition comprising live, non-pathogenic, synthetic bacterial mixture or live, non-pathogenic, purified or extracted, fecal microbiota, where the dose is administered at a dosing schedule of at least once or twice daily or at least once or twice weekly for at least three consecutive days or weeks. In another aspect, a dose is administered at least once, twice, or three times daily or at least once, twice, or three times daily for a period between 1 and 12 weeks, between 2 and 12 weeks, between 3 and 12 weeks, between 4 and 12 weeks, between 5 and 12 weeks, between 6 and 12 weeks, between 7 and 12 weeks, between 8 and 12 weeks, between 9 and 12 weeks, between 10 and 12 weeks, between 1 and 2 weeks, between 2 and 3 weeks, between 3 and 4 weeks, between 4 and 5 weeks, between 5 and 6 weeks, between 6 and 7 weeks, between 7 and 8 weeks, between 8 and 9 weeks, between 9 and 10 weeks, or between 10 and 11 weeks.

In one aspect, the present disclosure provides a method for treating recurrent diverticulitis in a subject in need thereof, where the method comprises a first dosing schedule followed by a second dosing schedule. In one aspect, a first dosing schedule comprises a treatment or induction dose. In one aspect, a first dosing schedule comprises a continuous dosing schedule. In another aspect, a second dosing schedule comprises a maintenance dose lower than or equal to a pharmaceutically active dose of a first dosing schedule. In another aspect, a second dosing schedule lasts for at least about 2, 4, 6, 8, 10, 12, 18, 24, 36, 48, 72, or 96 months. In one aspect, a second dosing schedule lasts permanently, for a treated subject's entire life span, or an indefinite period of time. In one aspect, a second dosing schedule is a continuous dosing schedule. In another aspect, a second dosing schedule is an intermittent dosing schedule. In a further aspect, a second dosing schedule is an intermittent dosing schedule comprising a treatment period of at least 1, 2, 3, 4, 5, 6, 7, 8, 9, 10, 11, 12, 13, or 14 days followed by a resting period of at least 1, 2, 3, 4, 5, 6, 7, 8, 9, 10, 11, 12, 13, or 14 days. In another aspect, a second dosing schedule comprises administering a second dose (e.g., a maintenance dose) every other day, every two days, or every 3, 4, 5, 6, 7, 8 days. In another aspect, a maintenance dose is administered for an extended period of time with or without titration (or otherwise changing the dosage or dosing schedule). In one aspect, the interval between a first and a second dosing schedule is at least about 1, 2, 3, 4, 5, 6, 7, 8, 9, 10, 11, or 12 weeks. In another aspect, a second dosing schedule (e.g., a maintenance dose) comprises a dosage about 2, 5, 10, 50, 100, 200, 400, 800, 1000, 5000 or more folds lower than the dosage used in a first dosing schedule (e.g., an initial treatment dose). In another aspect, a second dosing schedule (e.g., a maintenance dosing schedule) has an equal or lower dosing frequency than a first dosing schedule (e.g., an initial treatment dosing schedule). In another aspect, a second dosing schedule (e.g., a maintenance dosing schedule) has a higher dosing interval than a first dosing schedule (e.g., an initial treatment dosing schedule).

In one aspect, a first or second dosing schedule used in a method can be once-a-week, twice-a-week, or thrice-a-week. The term "once-a-week" means that a dose is administered once in a week, preferably on the same day of each week. "Twice-a-week" means that a dose is administered two times in a week, preferably on the same two days of each weekly period. "Thrice-a-week" means that a dose is administered three times in a week, preferably on the same three days of each weekly period.

In one aspect, a subject being treated is a subject already with recurrent diverticulitis. Administration of a disclosed therapeutic composition to clinically, asymptomatic human subject who is genetically predisposed or prone to recurrent diverticulitis is also useful in preventing the onset of clinical symptoms of recurrent diverticulitis. A human subject genetically predisposed or prone to recurrent diverticulitis can be a human subject having a close family member or relative exhibiting or having suffered recurrent diverticulitis. In another aspect, a subject being treated is a subject in which recurrent diverticulitis is to be prevented. In another aspect, a subject being treated is predisposed or susceptible to recurrent diverticulitis. In another aspect, a subject being treated is a subject diagnosed as having recurrent diverticulitis. In one aspect, a subject being treated is a patient in need of diverticulitis treatment. In another aspect, a patient being treated is immunocompromised. In another aspect, a patient being treated has both recurrent diverticulitis and IBD, IBS, or a *C. diff* infection.

In one aspect, a subject being treated has a stage I, stage II, stage III, or stage IV diverticulitis. In one aspect, the clinical staging of diverticulitis follows a modified Hinchey classification. Stage I is defined by the presence of a pericolic abscess. Stage II is defined by distant abscesses susceptible to percutaneous drainage. Stage III is defined by complex abscesses associated with a possible fistula. Stage IV is defined by fecal peritonitis. In another aspect, the clinical staging of diverticulitis follows Hinchey's classification as follows: Stage I: Diverticulitis with phlegmon or localized pericolic or mesenteric abscess; Stage II: Diverticulitis with walled-off pelvic, intra-abdominal, or retroperitoneal abscess; Stage III: Perforated diverticulitis causing generalized purulent peritonitis; and Stage IV: Rupture of diverticula into the peritoneal cavity with fecal contamination causing generalized fecal peritonitis.

In one aspect, a patient is subject to a treatment described here after being diagnosed with diverticulitis via computed tomography (CT) scanning of the abdomen. In another aspect, a diverticulitis patient treated here has a CT finding selected from the group consisting of pericolic fat stranding due to inflammation, colonic diverticula, bowel wall thickening, soft-tissue inflammatory masses, phlegmon, and abscesses. In one aspect, a diverticulitis patient treated here without requiring prior diagnosis via CT.

In one aspect, a subject being treated is a human patient. In one aspect, a patient is a male patient. In one aspect, a patient is a female patient. In one aspect, a patient is a premuature newborn. In one aspect, a patient is a term newborn. In one aspect, a patient is a neonate. In one aspect, a patient is an infant. In one aspect, a patient is a toddler. In one aspect, a patient is a young child. In one aspect, a patient is a child. In one aspect, a patient is an adolescent. In one aspect, a patient is a pediatric patient. In one aspect, a patient is a geriatric patient. In one aspect, a human patient is a child patient below about 18, 15, 12, 10, 8, 6, 4, 3, 2, or 1 year old. In another aspect, a human patient is an adult patient. In another aspect, a human patient is an elderly patient. In a further aspect, a human patient is a patient above about 30, 35, 40, 45, 50, 55, 60, 65, 70, 75, 80, 85, 90, or 95 years old. In another aspect, a patient is about between 1 and 5, between 2 and 10, between 3 and 18, between 21 and 50, between 21 and 40, between 21 and 30, between 50 and 90, between 60 and 90, between 70 and 90, between 60 and 80, or between 65 and 75 years old. In one aspect, a patient is a young old patient (65-74 years). In one aspect, a patient is a middle old patient (75-84 years). In one aspect, a patient is an old patient (>85 years).

In one aspect, a method comprises administering a therapeutic composition orally, by enema, or via rectal suppository. In one aspect, a therapeutic composition administered herein is formulated as an enteric coated (and/or acid-resistant) capsule or microcapsule, or formulated as part of or administered together with a food, a food additive, a dairy-based product, a soy-based product or a derivative thereof, a jelly, flavored liquid, ice block, ice-cream, or a yogurt. In another aspect, a therapeutic composition administered herein is formulated as an acid-resistant enteric coated capsule. A therapeutic composition can be provided as a powder for sale in combination with a food or drink. A food or drink can be a dairy-based product or a soy-based product. In another aspect, a food or food supplement contains enteric-coated and/or acid-resistant microcapsules containing a therapeutic composition.

In an aspect, a therapeutic composition comprises a liquid culture. In another aspect, a therapeutic composition is lyophilized, pulverized and powdered. It may then be infused, dissolved such as in saline, as an enema. Alternatively the powder may be encapsulated as enteric-coated and/or acid-resistant capsules for oral administration. These capsules may take the form of enteric-coated and/or acid-resistant microcapsules. A powder can preferably be provided in a palatable form for reconstitution for drinking or for reconstitution as a food additive. In a further aspect, a food is yogurt. In one aspect, a powder may be reconstituted to be infused via naso-duodenal infusion.

In another aspect, a therapeutic composition administered herein is in a liquid, frozen, freeze-dried, spray-dried, lyophilized, or powder form. In a further aspect, a therapeutic composition administered herein is formulated as a delayed or gradual enteric release form. In another aspect, a therapeutic composition administered herein comprises an excipient, a saline, a buffer, a buffering agent, or a fluid-glucose-cellobiose agar (RGCA) media. In another aspect, a therapeutic composition administered herein comprises a cryoprotectant. In one aspect, a cryoprotectant comprises polyethylene glycol, skim milk, erythritol, arabitol, sorbitol, glucose, fructose, alanine, glycine, proline, sucrose, lactose, ribose, trehalose, dimethyl sulfoxide (DMSO), glycerol, or a combination thereof.

In one aspect, a therapeutic composition administered herein further comprises an acid suppressant, an antacid, an H2 antagonist, a proton pump inhibitor or a combination thereof. In one aspect, a therapeutic composition administered herein substantially free of non-living matter. In another aspect, a therapeutic composition administered herein substantially free of acellular material selected from the group consisting of residual fiber, DNA, viral coat material, and non-viable material.

In one aspect, a therapeutic composition also comprises or is supplemented with a prebiotic nutrient selected from the group consisting of polyols, fructooligosaccharides (FOSs), oligofructoses, inulins, galactooligosaccharides (GOSs), xylooligosaccharides (XOSs), polydextroses, monosaccharides, tagatose, and/or mannooligosaccharides.

In one aspect, a method further comprises pretreating a subject with an antibiotic composition prior to administering a therapeutic bacterial or microbiota composition. In one aspect, an antibiotic composition administered herein comprises an antibiotic selected from the group consisting of rifabutin, clarithromycin, clofazimine, vancomycin, rifampicin, nitroimidazole, chloramphenicol, and a combination thereof. In another aspect, an antibiotic composition administered herein comprises an antibiotic selected from the group consisting of rifaximin, rifamycin derivative, rifampicin, rifabutin, rifapentine, rifalazil, bicozamycin, aminoglycoside, gentamycin, neomycin, streptomycin, paromomycin, verdamicin, mutamicin, sisomicin, netilmicin, retymicin, kanamycin, aztreonam, aztreonam macrolide, clarithromycin, dirithromycin, roxithromycin, telithromycin, azithromycin, bismuth subsalicylate, vancomycin, streptomycin, fidaxomicin, amikacin, arbekacin, neomycin, netilmicin, paromomycin, rhodostreptomycin, tobramycin, apramycin, and a combination thereof. In a further aspect, a method further comprises pretreating a subject with an anti-inflammatory drug prior to administration of a therapeutic bacterial or microbiota composition.

In one aspect, a method achieves a remission, cure, response, or resolution rate of recurrent diverticulitis of at least about 10%, 15%, 20%, 25%, 30%, 35%, 40%, 45%, 50%, 55%, 60%, 65%, 70%, 75%, 80%, 85%, 90%, 95%, 97%, or 99%. In one aspect, a treatment method described here reduces the recurrence frequency in a recurrent diverticulitis patient by at least 10%, 20%, 30%, 50%, 60%, 70%, 80%, or 90% in at least 10%, 20%, 30%, 50%, 60%, 70%, 80%, or 90% patients compared to baseline (e.g., immediately prior to treatment).

In one aspect, every about 200 mg of a pharmaceutical composition comprises a pharmacologically active dose. In one aspect, every about 75, 100, 125, 150, 175, 200, 250, 300, 350, 400, 450, 500, 750, 1000, 1500, or 2000 mg of a pharmaceutical composition comprises a pharmacologically active dose.

In one aspect, a pharmaceutically active or therapeutic effective dose comprises at least about $10^5$, $10^6$, $10^7$, $10^8$, $10^9$, $10^{10}$, $10^{11}$, $10^{12}$, or $10^{13}$ cfu. In another aspect, a pharmaceutically active therapeutic effective dose comprises at most about $10^5$, $10^6$, $10^7$, $10^8$, $10^9$, $10^{10}$, $10^{11}$, $10^{12}$, or $10^{13}$ cfu. In a further aspect, a pharmacologically active therapeutic effective dose is selected from the group consisting of from $10^8$ cfu to $10^{14}$ cfu, from $10^9$ cfu to $10^{13}$ cfu, from $10^{10}$ cfu to $10^{12}$ cfu, from $10^9$ cfu to $10^{14}$ cfu, from $10^9$ cfu to $10^{12}$ cfu, from $10^9$ cfu to $10^{11}$ cfu, from $10^9$ cfu to $10^{10}$ cfu, from $10^{10}$ cfu to $10^{14}$ cfu, from $10^{10}$ cfu to $10^{13}$ cfu, from $10^{11}$ cfu to $10^{14}$ cfu, from $10^{11}$ cfu to $10^{13}$ cfu, from $10^{12}$ cfu to $10^{14}$ cfu, and from $10^{13}$ cfu to $10^{14}$ cfu. In one aspect, a pharmaceutical composition comprises the foregoing pharmaceutically active or therapeutic effective dose in a unit weight of about 0.2, 0.4, 0.6, 0.8 or 1.0 gram, or a unit volume of about 0.2, 0.4, 0.6, 0.8 or 1.0 milliliter.

In one aspect, a pharmaceutically active or therapeutic effective dose comprises at least about $10^5$, $10^6$, $10^7$, $10^8$, $10^9$, $10^{10}$, $10^{11}$, $10^{12}$, or $10^{13}$ cells or spores. In another aspect, a pharmaceutically active or therapeutic effective dose comprises at most about $10^5$, $10^6$, $10^7$, $10^8$, $10^9$, $10^{10}$, $10^{11}$, $10^{12}$, or $10^{13}$ total cells or spores. In a further aspect, a pharmacologically active or therapeutic effective dose is selected from the group consisting of from $10^8$ to $10^{14}$, from $10^9$ to $10^{13}$, from $10^{10}$ to $10^{12}$, from $10^9$ to $10^{14}$, from $10^9$ to $10^{12}$, from $10^9$ to $10^{11}$, from $10^9$ to $10^{10}$, from $10^{10}$ to $10^{14}$, from $10^{10}$ to $10^{13}$, from $10^{11}$ to $10^{14}$, from $10^{11}$ to $10^{13}$, from $10^{12}$ to $10^{14}$, and from $10^{13}$ to $10^{14}$ cells or spores. In an aspect, the pharmaceutically active or therapeutic effective dose cell count is directed to live cells. In one aspect, a pharmaceutical composition comprises the foregoing pharmaceutically active or therapeutic effective dose in a unit weight of about 0.2, 0.4, 0.6, 0.8 or 1.0 gram, or a unit volume of about 0.2, 0.4, 0.6, 0.8 or 1.0 milliliter.

In one aspect, a therapeutic composition administered herein comprises fecal bacteria. In one aspect, a therapeutic composition administered herein comprises one or more, two or more, three or more, four or more, or five or more isolated, purified, or cultured microorganisms selected from the group consisting of *Clostridium, Bacillus, Collinsella, Bacteroides, Eubacterium, Fusobacterium, Propionibacterium, Lactobacillus, Ruminococcus, Escherichia coli, Gemmiger, Desulfomonas, Peptostreptococcus, Bifidobacterium, Coprococcus, Dorea,* and *Monilia.*

In one aspect, a therapeutic composition administered herein comprises at least one, at least two, at least three, at least four, at least five, at least six, or at least seven fecal microorganisms selected from the group consisting of a *Bacteroides fragilis* ssp. *vulgatus, Collinsella aerofaciens, Bacteroides fragilis* ssp. *thetaiotaomicron, Peptostreptococ-* cus productus II, Parabacteroides distasonis, Fusobacterium prausnitzii, Coprococcus eutactus, Collinsella aerofaciens III, Peptostreptococcus productus I, Ruminococcus bromii, Bifidobacterium adolescentis, Gemmiger formicilis, Bifidobacterium longum, Eubacterium siraeum, Ruminococcus torques, Eubacterium rectale, Eubacterium eligens, Bacteroides eggerthii, Clostridium leptum, Bacteroides fragilis ssp. A, Eubacterium biforme, Bifidobacterium infantis, Eubacterium rectale III-F, Coprococcus comes, Pseudoflavonifractor capillosus, Ruminococcus albus, Dorea formicigenerans, Eubacterium hallii, Eubacterium ventriosum I, Fusobacterium russi, Ruminococcus obeum, Eubacterium rectale, Clostridium ramosum, Lactobacillus leichmannii, Ruminococcus callidus, Butyrivibrio crossotus, Acidaminococcus fermentans, Eubacterium ventriosum, Bacteroides fragilis ssp. fragilis, Bacteroides AR, Coprococcus catus, Aerostipes hadrus, Eubacterium cylindroides, Eubacterium ruminantium, Eubacterium CH-1, Staphylococcus epidermidis, Peptostreptococcus BL, Eubacterium limosum, Tissirella praeacuta, Bacteroides L, Fusobacterium mortiferum I, Fusobacterium naviforme, Clostridium innocuum, Clostridium ramosum, Propionibacterium acnes, Ruminococcus flavefaciens, Ruminococcus AT, Peptococcus AU-1, Bacteroides fragilis ssp. ovatus, -ssp. d, -ssp. f; Bacteroides L-1, L-5; Fusobacterium nucleatum, Fusobacterium mortiferum, Escherichia coli, Gemella morbillorum, Finegoldia magnus, Peptococcus G, —AU-2; Streptococcus intermedius, Ruminococcus lactaris, Ruminococcus CO Gemmiger X, Coprococcus BH, —CC; Eubacterium tenue, Eubacterium ramulus, Bacteroides clostridiiformis ssp. clostridliformis, Bacteroides coagulans, Prevotella oralis, Prevotella ruminicola, Odoribacter splanchnicus, Desuifomonas pigra, Lactobacillus G, Succinivibrio A, and a combination thereof.

In one aspect, a therapeutic composition administered herein comprises no viable Bacteroides, Fusobacterium, Propionibacterium, Lactobacillus, Ruminococcus, Escherichia coli, Gemmiger, Desulfomonas, Peptostreptococcus, Bifidobacterium, Monilia, or any combination thereof. In another aspect, a therapeutic composition administered herein comprises no viable Bacteroides fragilis ssp. vulgatus, Collinsella aerofaciens, Bacteroides fragilis ssp. thetaiotaomicron, Peptostreptococcus productus II, Parabacteroides distasonis, Fusobacterium prausnitzii, Coprococcus eutactus, Collinsella aerofaciens III, Peptostreptococcus productus I, Ruminococcus bromii, Bifidobacterium adolescentis, Gemmiger formicilis, Bifidobacterium longum, Eubacterium siraeum, Ruminococcus torques, Eubacterium rectale, Eubacterium eligens, Bacteroides eggerthii, Clostridium leptum, Bacteroides fragilis ssp. A, Eubacterium biforme, Bifidobacterium infantis, Eubacterium rectale III-F, Coprococcus comes, Pseudollavonifractor capillosus, Ruminococcus albus, Dorea formicigenerans, Eubacterium hallii, Eubacterium ventriosum I, Fusobacterium russi, Ruminococcus obeum, Eubacterium rectale, Clostridium ramosum, Lactobacillus leichmannii, Ruminococcus callidus, Butyrivibrio crossotus, Acidaminococcus fermentans, Eubacterium ventriosum, Bacteroides fragilis ssp. fragilis, Bacteroides AR, Coprococcus catus, Aerostipes hadrus, Eubacterium cylindroides, Eubacterium ruminantium, Eubacterium CH-1, Staphylococcus epidermidis, Peptostreptococcus BL, Eubacterium limosum, Tissirella praeacuta, Bacteroides L, Fusobacterium mortiferum I, Fusobacterium naviforme, Clostridium innocuum, Clostridium ramosum, Propionibacterium acnes, Ruminococcus flavefaciens, Ruminococcus AT, Peptococcus AU-1, Bacteroides fragilis ssp. ovatus, -ssp. d, -ssp. f; Bacteroides L-1, L-5; Fusobacterium nucleatum, Fusobacterium mortiferum, Escherichia coli, Gemella morbillorum, Finegoldia magnus, Peptococcus G, —AU-2; Streptococcus intermedius, Ruminococcus lactaris, Ruminococcus CO Gemmiger X, Coprococcus BH, —CC; Eubacterium tenue, Eubacterium ramulus, Bacteroides clostridiiformis ssp. clostridliformis, Bacteroides coagulans, Prevotella oralis, Prevotella ruminicola, Odoribacter splanchnicus, Desuifomonas pigra, Lactobacillus G, Succinivibrio A, or a combination thereof.

In one aspect, a therapeutic composition administered herein comprises a fecal microbiota. In another aspect, the preparation of a fecal microbiota used herein involves a treatment selected from the group consisting of ethanol treatment, detergent treatment, heat treatment, irradiation, and sonication. In another aspect, the preparation of a fecal microbiota used herein involves no treatment selected from the group consisting of ethanol treatment, detergent treatment, heat treatment, irradiation, and sonication. In one aspect, the preparation of a fecal microbiota used herein involves a separation step selected from the group consisting of density gradients, filtration (e.g., sieves, nylon mesh), and chromatography. In another aspect, the preparation of a fecal microbiota used herein involves no separation step selected from the group consisting of density gradients, filtration (e.g., sieves, nylon mesh), and chromatography. In another aspect, a fecal microbiota used herein comprises a donor's entire fecal microbiota. In another aspect, a therapeutic composition administered herein comprises a fecal microbiota substantially free of eukaryotic cells from the fecal microbiota's donor.

In another aspect, a therapeutic composition administered herein comprises a fecal microbiota further supplemented, spiked, or enhanced with a fecal microorganism. In one aspect, a fecal microbiota is supplemented with a non-pathogenic (or with attenuated pathogenicity) bacterium of Clostridium, Collinsella, Dorea, Ruminococcus, Coprococcus, Prevotella, Veillonella, Bacteroides, Baccillus, or a combination thereof. In another aspect, a therapeutic composition administered herein comprises a fecal microbiota further supplemented, spiked, or enhanced with a species of Veillonellaceae, Firmicutes, Gammaproteobacteria, Bacteroidetes, or a combination thereof. In another aspect, a therapeutic composition administered herein comprises a fecal microbiota further supplemented with fecal bacterial spores. In one aspect, fecal bacterial spores are Clostridium spores, Bacillus spores, or both.

In an aspect, a therapeutic composition comprises a fecal microbiota from a subject selected from the group consisting of a human, a bovine, a dairy calf, a ruminant, an ovine, a caprine, or a cervine. In another aspect, a therapeutic composition can be administered to a subject selected from the group consisting of a human, a bovine, a dairy calf, a ruminant, an ovine, a caprine, or a cervine. In an aspect, a therapeutic composition is substantially or nearly odourless.

In an aspect, a therapeutic composition provided or administered herein comprises a fecal microbiota comprising a Shannon Diversity Index of greater than or equal to 0.3, greater than or equal to 0.4, greater than or equal to 0.5, greater than or equal to 0.6, greater than or equal to 0.7, greater than or equal to 0.8, greater than or equal to 0.9, greater than or equal to 1.0, greater than or equal to 1.1, greater than or equal to 1.2, greater than or equal to 1.3, greater than or equal to 1.4, greater than or equal to 1.5, greater than or equal to 1.6, greater than or equal to 1.7, greater than or equal to 1.8, greater than or equal to 1.9, greater than or equal to 2.0, greater than or equal to 2.1, greater than or equal to 2.2, greater than or equal to 2.3, greater than or equal to 2.4, greater than or equal to 2.5, greater than or equal to 3.0, greater than or equal to 3.1, greater than or equal to 3.2, greater than or equal to 3.3, greater than or equal to 3.4, greater than or equal to 3.5, greater than or equal to 3.6, greater than or equal to 3.7, greater than or equal to 3.8, greater than or equal to 3.9, greater than or equal to 4.0, greater than or equal to 4.1, greater than or equal to 4.2, greater than or equal to 4.3, greater than or equal to 4.4, greater than or equal to 4.5, or greater than or equal to 5.0. In another aspect, a therapeutic composition comprises fecal microbiota comprising a Shannon Diversity Index of between 0.1 and 3.0, between 0.1 and 2.5, between 0.1 and 2.4, between 0.1 and 2.3, between 0.1 and 2.2, between 0.1 and 2.1, between 0.1 and 2.0, between 0.4 and 2.5, between 0.4 and 3.0, between 0.5 and 5.0, between 0.7 and 5.0, between 0.9 and 5.0, between 1.1 and 5.0, between 1.3 and 5.0, between 1.5 and 5.0, between 1.7 and 5.0, between 1.9 and 5.0, between 2.1 and 5.0, between 2.3 and 5.0, between 2.5 and 5.0, between 2.7 and 5.0, between 2.9 and 5.0, between 3.1 and 5.0, between 3.3 and 5.0, between 3.5 and 5.0, between 3.7 and 5.0, between 31.9 and 5.0, or between 4.1 and 5.0. In one aspect, a Shannon Diversity Index is calculated at the phylum level. In another aspect, a Shannon Diversity Index is calculated at the family level. In one aspect, a Shannon Diversity Index is calculated at the genus level. In another aspect, a Shannon Diversity Index is calculated at the species level. In a further aspect, a therapeutic composition comprises a preparation of flora in proportional content that resembles a normal healthy human fecal flora.

In a further aspect, a therapeutic composition comprises fecal bacteria from at least 1, 2, 3, 4, 5, 6, 7, 8, 9, or 10 different families. In an aspect, a therapeutic composition provided or administered herein comprises a fecal microbiota comprising no greater than 0.05%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, or 10% weight non-living material/weight biological material. In another aspect, a therapeutic composition provided or administered herein comprises a fecal microbiota comprising no greater than 20%, 25%, 30%, 35%, 40%, 45%, 50%, 55%, 60%, 65%, 70%, 75%, 80%, 85%, 90%, or 95% weight non-living material/weight biological material. In another aspect, a therapeutic composition provided or administered herein comprises, consists of, or consists essentially of, particles of non-living material and/or particles of biological material of a fecal sample that passes through a sieve, a column, or a similar filtering device having a sieve, exclusion, or particle filter size of 2.0 mm, 1.0 mm, 0.33 mm, 0.5 mm, 0.25 mm, 0.212 mm, 0.180 mm, 0.150 mm, 0.125 mm, 0.106 mm, 0.090 mm, 0.075 mm, 0.063 mm, 0.053 mm, 0.045 mm, 0.038 mm, 0.032 mm, 0.025 mm, 0.020 mm, 0.01 mm, or 0.2 mm. "Non-living material" does not include an excipient, e.g., a pharmaceutically inactive substance, such as a cryoprotectant, added to a processed fecal material. "Biological material" refers to the living material in fecal material, and includes microbes including prokaryotic cells, such as bacteria and archaea (e.g., living prokaryotic cells and spores that can sporulate to become living prokaryotic cells), eukaryotic cells such as protozoa and fungi, and viruses. In one aspect, "biological material" refers to the living material, e.g., the microbes, eukaryotic cells, and viruses, which are present in the colon of a normal healthy human. In an aspect, a therapeutic composition provided or administered herein comprises an extract of human feces where the composition is substantially odorless. In an aspect, a therapeutic composition provided or administered herein comprises fecal material or a fecal floral preparation in a lyophilized, crude, semi-purified or purified formulation.

In an aspect, a fecal microbiota in a therapeutic composition comprises highly refined or purified fecal flora, e.g., substantially free of non-floral fecal material. In an aspect, a fecal microbiota can be further processed, e.g., to undergo microfiltration before, after, or before and after sieving. In another aspect, a highly purified fecal microbiota product is ultra-filtrated to remove large molecules but retain the therapeutic microflora, e.g., bacteria.

In another aspect, a fecal microbiota in a therapeutic composition used herein comprises or consists essentially of a substantially isolated or a purified fecal flora or entire (or substantially entire) microbiota that is (or comprises) an isolate of fecal flora that is at least about 90%, 91%, 92%, 93%, 94%, 95%, 96%, 97%, 98%, 99%, 99.5%, 99.6%, 99.7%, 99.8% or 99.9% isolated or pure, or having no more than about 0.1%, 0.2%, 0.3%, 0.4%, 0.5%, 0.6%, 0.7%, 0.8%, 0.9% or 1.0% or more non-fecal floral material; or, a substantially isolated, purified, or substantially entire microbiota as described in Sadowsky et al., WO 2012/122478 A1, or as described in Borody et al., WO 2012/016287 A2.

In an aspect, a fecal microbiota in a therapeutic composition comprises a donor's substantially entire or non-selected fecal microbiota, reconstituted fecal material, or synthetic fecal material. In another aspect, the fecal microbiota in a therapeutic composition comprises no antibiotic resistant population. In another aspect, a therapeutic composition comprises a fecal microbiota and is largely free of extraneous matter (e.g., non-living matter including acellular matter such as residual fiber, DNA, RNA, viral coat material, non-viable material; and living matter such as eukaryotic cells from the fecal matter's donor).

In an aspect, a fecal microbiota in a therapeutic composition used herein is derived from disease-screened fresh homologous feces or equivalent freeze-dried and reconstituted feces. In an aspect, a fresh homologous feces does not include an antibiotic resistant population. In another aspect, a fecal microbiota in a therapeutic composition is derived from a synthetic fecal composition. In an aspect, a synthetic fecal composition comprises a preparation of viable flora which preferably in proportional content, resembles normal healthy human fecal flora which does not include antibiotic resistant populations. Suitable microorganisms may be selected from the following: *Bacteroides, Eubacterium, Fusobacterium, Propionibacterium, Lactobacillus, Ruminococcus, Escherichia coli, Gemmiger, Clostridium, Desulfomonas, Peptostreptococcus, Bifidobacterium, Collinsella, Coprococcus, Dorea*, and *Ruminococcus*.

In an aspect, a therapeutic composition used in a treatment disclosed herein comprises a sterile fecal filtrate or a non-cellular fecal filtrate. In one aspect, a sterile fecal filtrate originates from a donor stool. In another aspect, a sterile fecal filtrate originates from cultured microorganisms. In another aspect, a sterile fecal filtrate comprises a non-cellular non-particulate fecal component. In one aspect, a sterile fecal filtrate is made as described in WO2014/078911, published May 30, 2014. In another aspect, a sterile fecal filtrate is made as described in Ott et al., *Gastroenterology* 152:799-911 (2017).

In one aspect, a fecal filtrate comprises secreted, execreted or otherwise liquid components or a microbiota, e.g., biologically active molecules (BAMs), which can be antibiotics or anti-inflammatories, are preserved, retained or reconstituted in a flora extract.

In one aspect, an exemplary therapeutic composition comprises starting material from a donor from a defined donor pool, where this donor contributes a stool that is centrifuged, then filtered with very high-level filtration using e.g., either metal sieving or Millipore filters, or equivalent, to ultimately permit only cells of bacterial origin to remain, e.g., often less than about 5 micrometres diameter. After the initial centrifugation, the solid material is separated from the liquid, and the solid is then filtered in progressively reducing size filters and tangential filters, e.g., using a Millipore filtration, and optionally, also comprising use of nano-membrane filtering. The filtering can also be done by sieves as described in WO 2012/122478, but in contrast using sieves that are smaller than 0.0120 mm, down to about 0.0110 mm, which ultimately result in having only bacterial cells present.

The supernatant separated during centrifugation is now taken and filtered progressively in a filtering, e.g., a Millipore filtering or equivalent systems, to end up with liquid which is finely filtered through an about 0.22 micron filter. This removes all particulate matter including all living matter, including bacteria and viruses. The product then is sterile, but the aim is to remove the bacteria but to keep their secretions, especially antimicrobial bacteriocins, bacteria-derived cytokine-like products and all accompanying Biologically Active Molecules (BAMs), including: thuricin (which is secreted by bacilli in donor stools), bacteriocins (including colicin, troudulixine or putaindicine, or microcin or subtilosin A), lanbiotics (including nisin, subtilin, epidermin, mutacin, mersacidin, actagardine, cinnamycin), lacticins and other antimicrobial or anti-inflammatory compounds.

In one aspect, a therapeutic composition used here comprises a reconstituted fecal flora consisting essentially of a combination of a purified fecal microbiota and a non-cellular fecal filtrate. In another aspect, a therapeutic composition used here comprises a purified fecal microbiota supplemented with one or more non-cellular non-particulate fecal components. In one aspect, a therapeutic composition used here comprises one or more non-cellular non-particulate fecal components. In one aspect, one or more non-cellular non-particulate fecal components comprise synthetic molecules, biologically active molecules produced by a fecal microorganism, or both. In another aspect, one or more non-cellular non-particulate fecal components comprise biologically active proteins or peptides, micronutrients, fats, sugars, small carbohydrates, trace elements, mineral salts, ash, mucous, amino acids, nutrients, vitamins, minerals, or any combination thereof. In one aspect, one or more non-cellular non-particulate fecal components comprise one or more biologically active molecules selected from the group consisting of bacteriocin, lanbiotic, and lacticin. In another aspect, one or more non-cellular non-particulate fecal components comprise one or more bacteriocins selected from the group consisting of colicin, troudulixine, putaindicine, microcin, and subtilosin A. In one aspect, one or more non-cellular non-particulate fecal components comprise one or more lanbiotics selected from the group consisting of thuricin, nisin, subtilin, epidermin, mutacin, mersacidin, actagardine, and cinnamycin. In another aspect, one or more non-cellular non-particulate fecal components comprise an anti-spore compound, an antimicrobial compound, an anti-inflammatory compound, or any combination thereof. In a further aspect, one or more non-cellular non-particulate fecal components comprise an interleukin, a cytokine, a leukotriene, an eicosanoid, or any combination thereof.

In another aspect, a treatment method provided here comprises the use of both fecal bacterial cells, e.g., a partial or a complete representation of the human GI microbiota, and an isolated, processed, filtered, concentrated, reconstituted and/or artificial liquid component (e.g., fecal filtrate) of the flora (the microbiota) which comprises, among others ingredients, bacterial secretory products such as e.g., bacteriocins (proteinaceous toxins produced by bacteria, including colicin, troudulixine or putaindicine, or microcin or subtilosin A), lanbiotics (a class of peptide antibiotics that contain a characteristic polycyclic thioether amino acid lanthionine or methyllanthionine, and unsaturated amino acids dehydroalanine and 2-aminoisobutyric acid; which include thuricin (which is secreted by bacilli in donor stools), nisin, subtilin, epidermin, mutacin, mersacidin, actagardine, cinnamycin), a lacticin (a family of pore-forming peptidic toxins) and other antimicrobial or anti-inflammatory compounds and/or additional biologically active molecules (BAMs) produced by bacteria or other microorganisms of the microbiota, and/or which are found in the "liquid component" of a microbiota.

In one aspect, a fecal bacteria-based therapeutic composition is used concurrently with a fecal non-cellular filtrate-based therapeutic composition. In another aspect, a patient is treated with a first fecal non-cellular filtrate-based therapeutic composition before being given a second fecal bacteria-based therapeutic composition, or vice versa. In a further aspect, a treatment method comprises three steps: first, antibiotic pre-treatment to non-selectively remove infectious pathogen(s); second, a fecal non-cellular filtrate-based treatment step to further suppress selected infectious pathogen (s); and third, giving the patient a fecal bacteria-based therapeutic composition to re-establish a functional intestinal microbiome.

In an aspect, a therapeutic composition is combined with other adjuvants such as antacids to dampen bacterial inactivation in the stomach. (e.g., Mylanta, Mucaine, Gastrogel). In another aspect, acid secretion in the stomach could also be pharmacologically suppressed using H2-antagonists or proton pump inhibitors. An example H2-antagonist is ranitidine. An example proton pump inhibitor is omeprazole. In one aspect, an acid suppressant is administered prior to administering, or in co-administration with, a therapeutic composition.

In an aspect, a therapeutic composition is in the form of: an enema composition which can be reconstituted with an appropriate diluent; enteric-coated capsules; enteric-coated microcapsules; acid-resistant tablet; acid-resistant capsules; acid-resistant microcapsules; powder for reconstitution with an appropriate diluent for naso-enteric infusion or colonoscopic infusion; powder for reconstitution with appropriate diluent, flavoring and gastric acid suppression agent for oral ingestion; powder for reconstitution with food or drink; or food or food supplement comprising enteric-coated and/or acid-resistant microcapsules of the composition, powder, jelly, or liquid.

In an aspect, a treatment method effects a cure, reduction of the symptoms, or a percentage reduction of symptoms of recurrent diverticulitis. The change of flora is preferably as "near-complete" as possible and the flora is replaced by viable organisms which will crowd out any remaining, original flora. Typically the change in enteric flora comprises introduction of an array of predetermined flora into the gastro-intestinal system, and thus in a preferred form the method of treatment comprises substantially or completely displacing pathogenic enteric flora in patients requiring such treatment.

In another aspect, a therapeutic composition can be provided together with a pharmaceutically acceptable carrier. As used herein, a "pharmaceutically acceptable carrier"

refers to a non-toxic solvent, dispersant, excipient, adjuvant, or other material which is mixed with a live bacterium in order to permit the formation of a pharmaceutical composition, e.g., a dosage form capable of administration to the patient. A pharmaceutically acceptable carrier can be liquid (e.g., saline), gel or solid form of diluents, adjuvant, excipients or an acid resistant encapsulated ingredient. Suitable diluents and excipients include pharmaceutical grades of physiological saline, dextrose, glycerol, mannitol, lactose, starch, magnesium stearate, sodium saccharin, cellulose, magnesium carbonate, and the like, and combinations thereof. In another aspect, a therapeutic composition may contain auxiliary substances such as wetting or emulsifying agents, stabilizing or pH buffering agents. In an aspect, a therapeutic composition contains about 1%-5%, 5%-10%, 10%-15%, 15-20%, 20%-25%, 25-30%, 30-35%, 40-45%, 50%-55%, 1%-95%, 2%-95%, 5%-95%, 10%-95%, 15%-95%, 20%-95%, 25%-95%, 30%-95%, 35%-95%, 40%-95%, 45%-95%, 50%-95%, 55%-95%, 60%-95%, 65%-95%, 70%-95%, 45%-95%, 80%-95%, or 85%-95% of active ingredient. In an aspect, a therapeutic composition contains about 2%-70%, 5%-60%, 10%-50%, 15%-40%, 20%-30%, 25%-60%, 30%-60%, or 35%-60% of active ingredient.

In an aspect, a therapeutic composition can be incorporated into tablets, drenches, boluses, capsules or premixes. Formulation of these active ingredients into such dosage forms can be accomplished by means of methods well known in the pharmaceutical formulation arts. See, e.g., U.S. Pat. No. 4,394,377. Filling gelatin capsules with any desired form of the active ingredients readily produces capsules. If desired, these materials can be diluted with an inert powdered diluent, such as sugar, starch, powdered milk, purified crystalline cellulose, or the like to increase the volume for convenience of filling capsules.

In an aspect, conventional formulation processes can be used to prepare tablets containing a therapeutic composition. In addition to the active ingredients, tablets may contain a base, a disintegrator, an absorbent, a binder, and a lubricant. Typical bases include lactose, sugar, sodium chloride, starch and mannitol. Starch is also a good disintegrator as is alginic acid. Surface-active agents such as sodium lauryl sulfate and dioctyl sodium sulphosuccinate are also sometimes used. Commonly used absorbents include starch and lactose. Magnesium carbonate is also useful for oily substances. As a binder there can be used, for example, gelatin, gums, starch, dextrin, polyvinyl pyrrolidone and various cellulose derivatives. Among the commonly used lubricants are magnesium stearate, talc, paraffin wax, various metallic soaps, and polyethylene glycol.

In an aspect, for preparing solid compositions such as tablets, an active ingredient is mixed with a pharmaceutical carrier, e.g., conventional tableting ingredients such as corn starch, lactose, sucrose, sorbitol, talc, stearic acid, magnesium stearate, dicalcium phosphate or gums, or other pharmaceutical diluents, e.g. water, to form a solid preformulation composition containing a homogeneous mixture of a composition of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing a desired amount of an active ingredient (e.g., at least about $10^5$, $10^6$, $10^7$, $10^8$, $10^9$, $10^{10}$, $10^{11}$, $10^{12}$, or $10^{13}$ cfu or total cell count). A therapeutic composition used herein can be flavored.

In an aspect, a therapeutic composition can be a tablet or a pill. In one aspect, a tablet or a pill can be coated or otherwise compounded to provide a dosage form affording the advantage of prolonged action. For example, a tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

In an aspect, a therapeutic composition can be a drench. In one aspect, a drench is prepared by choosing a saline-suspended form of a therapeutic composition. A water-soluble form of one ingredient can be used in conjunction with a water-insoluble form of the other by preparing a suspension of one with an aqueous solution of the other. Water-insoluble forms of either active ingredient may be prepared as a suspension or in some physiologically acceptable solvent such as polyethylene glycol. Suspensions of water-insoluble forms of either active ingredient can be prepared in oils such as peanut, corn, sesame oil or the like; in a glycol such as propylene glycol or a polyethylene glycol; or in water depending on the solubility of a particular active ingredient. Suitable physiologically acceptable adjuvants may be necessary in order to keep the active ingredients suspended. Adjuvants can include and be chosen from among the thickeners, such as carboxymethylcellulose, polyvinyl pyrrolidone, gelatin and the alginates. Surfactants generally will serve to suspend the active ingredients, particularly the fat-soluble propionate-enhancing compounds. Most useful for making suspensions in liquid nonsolvents are alkylphenol polyethylene oxide adducts, naphthalene-sulfonates, alkylbenzene-sulfonates, and the polyoxyethylene sorbitan esters. In addition many substances, which affect the hydrophilicity, density and surface tension of the liquid, can assist in making suspensions in individual cases. For example, silicone anti-foams, glycols, sorbitol, and sugars can be useful suspending agents.

In an aspect, a therapeutic composition comprises non-pathogenic spores of one or more, two or more, three or more, or four or more *Clostridium* species selected from the group consisting of *Clostridium absonum, Clostridium argentinense, Clostridium baratii, Clostridium botulinum, Clostridium cadaveris, Clostridium carnis, Clostridium celatum, Clostridium chauvoei, Clostridium clostridioforme, Clostridium cochlearium, Clostridium fallax, Clostridium felsineum, Clostridium ghonii, Clostridium glycolicum, Clostridium haemolyticum, Clostridium hastiforme, Clostridium histolyticum, Clostridium indolis, Clostridium irregulare, Clostridium limosum, Clostridium malenominatum, Clostridium novyi, Clostridium oroticum, Clostridium paraputrificum, Clostridium perfringens, Clostridium piliforme, Clostridium putrefaciens, Clostridium putrificum, Clostridium sardiniense, Clostridium sartagoforme, Clostridium scindens, Clostridium septicum, Clostridium sordellii, Clostridium sphenoides, Clostridium spiroforme, Clostridium sporogenes, Clostridium sub terminale, Clostridium symbiosum, Clostridium tertium, Clostridium tetani, Clostridium welchii,* and *Clostridium villosum.*

In an aspect, a therapeutic composition comprises purified, isolated, or cultured viable non-pathogenic *Clostridium* and a plurality of purified, isolated, or cultured viable non-pathogenic microorganisms from one or more genera selected from the group consisting of *Collinsella, Coprococcus, Dorea, Eubacterium*, and *Ruminococcus*. In another aspect, a therapeutic composition comprises a plurality of purified, isolated, or cultured viable non-pathogenic microorganisms from one or more genera selected from the group consisting of *Clostridium, Collinsella, Coprococcus, Dorea, Eubacterium*, and *Ruminococcus*.

In an aspect, a therapeutic composition comprises two or more genera selected from the group consisting of *Collinsella, Coprococcus, Dorea, Eubacterium*, and *Ruminococcus*. In another aspect, a therapeutic composition comprises two or more genera selected from the group consisting of *Coprococcus, Dorea, Eubacterium*, and *Ruminococcus*. In a further aspect, a therapeutic composition comprises one or more, two or more, three or more, four or more, or five or more species selected from the group consisting of *Coprococcus catus, Coprococcus comes, Dorea longicatena, Eubacterium eligens, Eubacterium hadrum, Eubacterium hallii, Eubacterium rectale*, and *Ruminococcus torques*.

In one aspect, a therapeutic composition comprises at least about $10^5$, $10^6$, $10^7$, $10^8$, $10^9$, $10^{10}$, $10^{11}$, $10^{12}$, or $10^{13}$ cfu or total cell count. In another aspect, a therapeutic composition comprises at most about $10^5$, $10^6$, $10^7$, $10^8$, $10^9$, $10^{10}$, $10^{11}$, $10^{12}$, $10^{13}$, or $10^{14}$ cfu or total cell count.

In another aspect, a therapeutic composition comprises at least about $10^5$, $10^6$, $10^7$, $10^8$, $10^9$, $10^{10}$, $10^{11}$, $10^{12}$, or $10^{13}$ cells or total cell count. In another aspect, a therapeutic composition comprises at most about $10^5$, $10^6$, $10^7$, $10^8$, $10^9$, $10^{10}$, $10^{11}$, $10^{12}$, $10^{13}$ or $10^{14}$ cells or total cell count.

In one aspect, a therapeutic composition is formulated as an oral capsule, microcapsule, tablet, or pill. In another aspect, a capsule, microcapsule, tablet, or pill is adapted for enteric delivery. In a further aspect, a capsule, microcapsule, tablet, or pill is an enteric capsule, microcapsule, tablet, or pill. In another aspect, a capsule, microcapsule, tablet, or pill comprises an enteric coating, is acid resistant, or both.

In one aspect, this application provides for the following embodiments:

Embodiment 1. A method for treating recurrent diverticulitis in a subject in need thereof, said method comprising administering to said subject a pharmaceutically active dose of a therapeutic composition comprising live non-pathogenic fecal bacteria or a non-cellular fecal filtrate.

Embodiment 2. The method of claim 1, wherein said recurrent diverticulitis is at a clinical stage selected from the group consisting of Stages I to IV.

Embodiment 3. The method of claim 1, wherein said composition comprises an isolated or purified population of said live non-pathogenic fecal bacteria.

Embodiment 4. The method of claim 1, wherein said composition comprises a non-selected fecal microbiota.

Embodiment 5. The method of claim 1, wherein said administration is on a daily basis.

Embodiment 6. The method of claim 1, wherein said administration lasts at least 1, 2, 3, 4, 5, 6, 7, 8, 9, or 10 weeks.

Embodiment 7. The method of claim 1, wherein said dose is administered at least once daily or at least once weekly for at least 2, 3, 4, 5, 6, 7, 8, 9, 10, 11, 12, 13, 14, or 15 consecutive days or weeks.

Embodiment 8. The method of claim 1, wherein said dose is administered at least once daily or at least once weekly for at least 1, 2, 3, 4, 5, 6, 7, 8, 9, 10, 11, or 12 consecutive weeks.

Embodiment 9. The method of claim 1, wherein said dose is administered at least once daily or at least once weekly for at most 3, 4, 5, 6, 7, 8, 9, 10, 11, 12, 13, 14, 15, 16, 17, 18, 19, or 20 consecutive days or weeks.

Embodiment 10. The method of claim 1, wherein said dose is administered at least once daily or at least once weekly for at most 1, 2, 3, 4, 5, 6, 7, 8, 9, 10, 11, or 12 consecutive weeks.

Embodiment 11. The method of claim 1, wherein said dose is administered at least twice daily or at least twice weekly for at least two consecutive days or weeks.

Embodiment 12. The method of claim 11, wherein said dose is administered at least twice daily or at least twice weekly for at least 3, 4, 5, 6, 7, 8, 9, 10, 11, 12, 13, 14, or 15 consecutive days or weeks.

Embodiment 13. The method of claim 11, wherein said dose is administered at least twice daily or at least twice weekly for at least 1, 2, 3, 4, 5, 6, 7, 8, 9, 10, 11, or 12 consecutive weeks.

Embodiment 14. The method of claim 11, wherein said dose is administered at least twice daily or at least twice weekly for at most 3, 4, 5, 6, 7, 8, 9, 10, 11, 12, 13, 14, 15, 16, 17, 18, 19, or 20 consecutive days or weeks.

Embodiment 15. The method of claim 11, wherein said dose is administered at least twice daily or at least twice weekly for at most 1, 2, 3, 4, 5, 6, 7, 8, 9, 10, 11, or 12 consecutive weeks.

Embodiment 16. The method of claim 1, wherein said dose is administered at least three times daily or at least three times weekly for at least one day or week.

Embodiment 17. The method of claim 16, wherein said dose is administered at least three times daily or at least three times weekly for at least 2, 3, 4, 5, 6, 7, 8, 9, 10, 11, 12, 13, 14, or 15 consecutive days or weeks.

Embodiment 18. The method of claim 16, wherein said dose is administered at least three times daily or at least three times weekly for at most 2, 3, 4, 5, 6, 7, 8, 9, 10, 11, 12, 13, 14, or 15 consecutive days or weeks.

Embodiment 19. The method of claim 1, wherein therapeutic composition comprising both live non-pathogenic fecal bacteria and a non-cellular fecal filtrate.

Embodiment 20. The method of claim 1, wherein therapeutic composition comprising live non-pathogenic fecal bacteria supplemented with a non-cellular fecal filtrate.

Embodiment 21. The method of claim 1, 19, or 20, wherein said non-cellular fecal filtrate comprises biologically active proteins or peptides, micronutrients, fats, sugars, small carbohydrates, trace elements, mineral salts, ash, mucous, amino acids, nutrients, vitamins, minerals, or any combination thereof.

Embodiment 22. The method of claim 1, 19, or 20, wherein said non-cellular fecal filtrate comprises one or more biologically active molecules selected from the group consisting of bacteriocin, lanbiotic, and lacticin.e Embodiment 23. The method of claim 1, 19, or 20, wherein said non-cellular fecal filtrate comprises one or more bacteriocins selected from the group consisting of colicin, troudulixine, putaindicine, microcin, and subtilosin A.

Embodiment 24. The method of claim 1, 19, or 20, wherein said non-cellular fecal filtrate comprises one or more lanbiotics selected from the group consisting of thuricin, nisin, subtilin, epidermin, mutacin, mersacidin, actagardine, and cinnamycin.

Embodiment 25. The method of claim 1, 19, or 20, wherein said non-cellular fecal filtrate comprises an anti-spore compound, an antimicrobial compound, an anti-inflammatory compound, or any combination thereof.

Embodiment 26. The method of claim 1, 19, or 20, wherein said non-cellular fecal filtrate comprises an interleukin, a cytokine, a leukotriene, an eicosanoid, or any combination thereof.

Embodiment 27. The method of any one of preceding claims, wherein said method comprises a first dosing schedule followed by a second dosing schedule.

Embodiment 28. The method of claim 27, wherein said second dosing schedule comprises a maintenance dose lower or equal to the dose of said first dosing schedule.

Embodiment 29. The method of claim 28, wherein said second dosing schedule lasts for at least about 2, 4, 6, 8, 10, 12, 18, 24, 36, 48, 72, or 96 months.

Embodiment 30. The method of claim 28, wherein said second dosing schedule lasts permanently.

Embodiment 31. The method of claim 27, wherein the interval between said first and second dosing schedules is at least about 1, 2, 3, 4, 5, 6, 7, 8, 9, 10, 11, or 12 weeks.

Embodiment 32. The method of claim 27, wherein said second dosing schedule is an continuous dosing schedule.

Embodiment 33. The method of claim 27, wherein said second dosing schedule is an intermittent dosing schedule.

Embodiment 34. The method of claim 33, wherein said intermittent dosing schedule comprises a treatment period of at least 1, 2, 3, 4, 5, 6, 7, 8, 9, 10, 11, 12, 13, or 14 days followed by a resting period of at least 1, 2, 3, 4, 5, 6, 7, 8, 9, 10, 11, 12, 13, or 14 days.

Embodiment 35. The method of any one of preceding claims, wherein said composition is formulated as a delayed or gradual enteric release form.

Embodiment 36. The method of any one of preceding claims, wherein said administering comprises administering orally, by enema, or via rectal suppository.

Embodiment 37. The method of any one of preceding claims, wherein said composition is formulated as an enteric coated capsule, an acid-resistant, enteric-coated capsule, an enteric coated microcapsule, or formulated as part of a food, a food additive, a dairy-based product, a soy-based product or a derivative thereof, a jelly, or a yogurt.

Embodiment 38. The method of any one of preceding claims, wherein said method eliminates or reduces gastrointestinal dysbiosis.

Embodiment 39. The method of any one of preceding claims, wherein said method increase bacterial diversity in said subject's gastrointestinal tract.

Embodiment 40. The method of any one of preceding claims, wherein said pharmaceutically active dose comprises at least about $10^5$, $10^6$, $10^7$, $10^8$, $10^9$, $10^{10}$, $10^{11}$, $10^{12}$, or $10^{13}$ cfu or total number of cells.

Embodiment 41. The method of claim 1, wherein said pharmaceutically active dose comprises at most about $10^5$, $10^6$, $10^7$, $10^8$, $10^9$, $10^{10}$, $10^{11}$, $10^{12}$, or $10^{13}$ cfu or total number of cells.

Embodiment 42. The method of claim 1, wherein said pharmaceutically active dose is selected from the group consisting of from $10^5$ to $10^{14}$, from $10^6$ to $10^{14}$, from $10^7$ to $10^{14}$, from $10^8$ to $10^{14}$, from $10^9$ to $10^{13}$, from $10^{10}$ to $10^{12}$, from $10^9$ to $10^{14}$, from $10^9$ to $10^{12}$, from $10^9$ to $10^{11}$, from $10^9$ to $10^{10}$, from $10^{10}$ to $10^{14}$, from $10^{10}$ to $10^{13}$, from $10^{11}$ to $10^{14}$, from $10^{11}$ to $10^{13}$, from $10^{12}$ to $10^{14}$, and from $10^{13}$ to $10^{14}$ cfu or total number of cells.

Embodiment 43. The method of claim 1, wherein said composition comprises a fecal microbiota further supplemented with a fecal microorganism.

Embodiment 44. The method of claim 43, wherein said fecal microorganism is selected from the group consisting of a *Bacteroides fragilis* ssp. *vulgatus, Collinsella aerofaciens, Bacteroides fragilis* ssp. *thetaiotaomicron, Peptostreptococcus productus* II, *Parabacteroides distasonis, Fusobacterium prausnitzii, Coprococcus eutactus, Collinsella aerofaciens* III, *Peptostreptococcus productus* I, *Ruminococcus bromii, Bifidobacterium adolescentis, Gemmiger formicilis, Bifidobacterium longum, Eubacterium siraeum, Ruminococcus torques, Eubacterium rectale, Eubacterium eligens, Bacteroides eggerthii, Clostridium leptum, Bacteroides fragilis* ssp. A, *Eubacterium biforme, Bifidobacterium infantis, Eubacterium rectale* III-F, *Coprococcus comes, Pseudoflavonifractor capillosus, Ruminococcus albus, Dorea formicigenerans, Eubacterium hallii, Eubacterium ventriosum* I, *Fusobacterium russi, Ruminococcus obeum, Eubacterium rectale, Clostridium ramosum, Lactobacillus leichmannii, Ruminococcus callidus, Butyrivibrio crossotus, Acidaminococcus fermentans, Eubacterium ventriosum, Bacteroides fragilis* ssp. *fragilis, Bacteroides* AR, *Coprococcus catus, Aerostipes hadrus, Eubacterium cylindroides, Eubacterium ruminantium, Eubacterium* CH-1, *Staphylococcus epidermidis, Peptostreptococcus* BL, *Eubacterium limosum, Tissirella praeacuta, Bacteroides* L, *Fusobacterium mortiferum* I, *Fusobacterium naviforme, Clostridium innocuum, Clostridium ramosum, Propionibacterium acnes, Ruminococcus flavefaciens, Ruminococcus* AT, *Peptococcus* AU-1, *Bacteroides fragilis* ssp. *ovatus,* -ssp. d, -ssp. f; *Bacteroides* L-1, L-5; *Fusobacterium nucleatum, Fusobacterium mortiferum, Escherichia coli, Gemella morbillorum, Finegoldia magnus, Peptococcus* G, —AU-2; *Streptococcus intermedius, Ruminococcus lactaris, Ruminococcus* CO *Gemmiger* X, *Coprococcus* BH, —CC; *Eubacterium tenue, Eubacterium ramulus, Bacteroides clostridiiformis* ssp. *clostridliformis, Bacteroides coagulans, Prevotella oralis, Prevotella ruminicola, Odoribacter splanchnicus, Desuifomonas pigra, Lactobacillus* G, *Succinivibrio* A, and a combination thereof.

Embodiment 45. The method of claim 4, wherein said fecal microbiota is further supplemented with bacterial spores.

Embodiment 46. The method of claim 45, wherein said bacterial spores are *Clostridium* spores or *Bacillus* spores.

Embodiment 47. The method of claim 4, wherein the preparation of said fecal microbiota involves a treatment selected from the group consisting of ethanol treatment, detergent treatment, heat treatment, irradiation, and sonication.

Embodiment 48. The method of claim 4, wherein the preparation of said fecal microbiota involves no treatment selected from the group consisting of ethanol treatment, detergent treatment, heat treatment, irradiation, and sonication.

Embodiment 49. The method of claim 4, wherein the preparation of said fecal microbiota involves a separation step selected from the group consisting of density gradients, filtration, and chromatography.

Embodiment 50. The method of claim 4, wherein the preparation of said fecal microbiota involves no separation step selected from the group consisting of density gradients, filtration, and chromatography.

Embodiment 51. The method of claim 4, wherein said fecal microbiota comprises a donor's entire fecal microbiota.

Embodiment 52. The method of claim 4, wherein said composition is substantially free of eukaryotic cells from said fecal microbiota's donor.

Embodiment 53. The method of claim 4, wherein said fecal microbiota is from reconstituted fecal material.

Embodiment 54. The method of claim 4, wherein said fecal microbiota is from synthetic fecal material.

Embodiment 55. The method of claim 4, wherein said fecal microbiota comprises no antibiotic resistant population.

Embodiment 56. The method of claim 4, wherein said fecal microbiota comprises a preparation of viable flora in proportional content that resembles a normal healthy human fecal flora.

Embodiment 57. The method of claim 4, wherein said fecal microbiota comprises bacteria from at least seven different families.

Embodiment 58. The method of claim 4, wherein said fecal microbiota has a Shannon Diversity Index of 0.4-5.0.

Embodiment 59. The method of claim 4, wherein said fecal microbiota comprises one or more microorganisms selected from the group consisting of *Clostridium, Bacillus, Collinsella, Bacteroides, Eubacterium, Fusobacterium, Propionibacterium, Lactobacillus, Ruminococcus, Escherichia coli, Gemmiger, Desulfomonas, Peptostreptococcus, Bifidobacterium*, and *Monilia*.

Embodiment 60. The method of claim 4, wherein said fecal microbiota comprises no viable *Bacteroides, Fusobacterium, Propionibacterium, Lactobacillus, Ruminococcus, Escherichia coli, Gemmiger, Desulfomonas, Peptostreptococcus, Bifidobacterium, Monilia*, or any combination thereof.

Embodiment 61. The method of claim 4, wherein said fecal microbiota comprises one or more microorganisms selected from the group consisting of a *Bacteroides fragilis* ssp. *vulgatus, Collinsella aerofaciens, Bacteroides fragilis* ssp. *thetaiotaomicron, Peptostreptococcus productus* II, *Parabacteroides distasonis, Fusobacterium prausnitzii, Coprococcus eutactus, Collinsella aerofaciens* III, *Peptostreptococcus productus* I, *Ruminococcus bromii, Bifidobacterium adolescentis, Gemmiger formicilis, Bifidobacterium longum, Eubacterium siraeum, Ruminococcus torques, Eubacterium rectale, Eubacterium eligens, Bacteroides eggerthii, Clostridium leptum, Bacteroides fragilis* ssp. *A, Eubacterium biforme, Bifidobacterium infantis, Eubacterium rectale* III-F, *Coprococcus comes, Pseudoflavonifractor capillosus, Ruminococcus albus, Dorea formicigenerans, Eubacterium hallii, Eubacterium ventriosum* I, *Fusobacterium russi, Ruminococcus obeum, Eubacterium rectale, Clostridium ramosum, Lactobacillus leichmannii, Ruminococcus callidus, Butyrivibrio crossotus, Acidaminococcus fermentans, Eubacterium ventriosum, Bacteroides fragilis* ssp. *fragilis, Bacteroides* AR, *Coprococcus catus, Aerostipes hadrus, Eubacterium cylindroides, Eubacterium ruminantium, Eubacterium* CH-1, *Staphylococcus epidermidis, Peptostreptococcus* BL, *Eubacterium limosum, Tissirella praeacuta, Bacteroides* L, *Fusobacterium mortiferum* I, *Fusobacterium naviforme, Clostridium innocuum, Clostridium ramosum, Propionibacterium acnes, Ruminococcus flavefaciens, Ruminococcus* AT, *Peptococcus* AU-1, *Bacteroides fragilis* ssp. *ovatus*, -ssp. d, -ssp. f; *Bacteroides* L-1, L-5; *Fusobacterium nucleatum, Fusobacterium mortiferum, Escherichia coli, Gemella morbillorum, Finegoldia magnus, Peptococcus* G, —AU-2; *Streptococcus intermedius, Ruminococcus lactaris, Ruminococcus* CO *Gemmiger* X, *Coprococcus* BH, —CC; *Eubacterium tenue, Eubacterium ramulus, Bacteroides clostridiiformis* ssp. *clostridliformis, Bacteroides coagulans, Prevotella oralis, Prevotella ruminicola, Odoribacter splanchnicus, Desuifomonas pigra, Lactobacillus* G, *Succinivibrio* A, and a combination thereof.

Embodiment 62. The method of claim 1, wherein said composition comprises at least about 20%, 30%, 40%, 50%, 60%, 70%, 80%, 85%, 90%, 95%, 99%, or 99.5% bacterial spores.

Embodiment 63. The method of claim 1, wherein said composition is in a liquid, frozen, freeze-dried, spray-dried, lyophilized, or powder form.

Embodiment 64. The method of claim 1, wherein said composition comprises an excipient, a saline, a buffer, a buffering agent, or a fluid-glucose-cellobiose agar (RGCA) media.

Embodiment 65. The method of claim 1, wherein said composition comprises a cryoprotectant.

Embodiment 66. The method of claim 65, wherein said cryoprotectant comprises polyethylene glycol, skim milk, erythritol, arabitol, sorbitol, glucose, fructose, alanine, glycine, proline, sucrose, lactose, ribose, trehalose, dimethyl sulfoxide (DMSO), glycerol, or a combination thereof.

Embodiment 67. The method of claim 1, wherein said composition further comprises an acid suppressant, an antacid, an H2 antagonist, a proton pump inhibitor or a combination thereof.

Embodiment 68. The method of claim 1, wherein said composition is substantially free of non-living matter.

Embodiment 69. The method of claim 1, wherein said composition is substantially free of acellular material selected from the group consisting of residual fiber, DNA, viral coat material, and non-viable material.

Embodiment 70. The method of claim 1, wherein said composition is formulated as an enteric coated capsule or microcapsule, an acid-resistant capsule or microcapsule, a powder suitable for reconstitution, a naso-duodenal infusion, or for delivery in the form of an enema or a colonoscopic infusion.

Embodiment 71. The method of claim 1, wherein said composition is administered together with a food, a liquid beverage, a food additive, a dairy-based product, a soy-based product or a derivative thereof, a jelly, or a yogurt.

Embodiment 72. The method of claim 1, wherein said subject is pretreated with an antibiotic prior to administration of said composition.

Embodiment 73. The method of claim 72, wherein said antibiotic is selected from the group consisting of rifabutin, clarithromycin, clofazimine, vancomycin, rifampicin, nitroimidazole, chloramphenicol, and a combination thereof.

Embodiment 74. The method of claim 72, wherein said antibiotic is selected from the group consisting of rifaximin, rifamycin derivative, rifampicin, rifabutin, rifapentine, rifalazil, bicozamycin, aminoglycoside, gentamycin, neomycin, streptomycin, paromomycin, verdamicin, mutamicin, sisomicin, netilmicin, retymicin, kanamycin, aztreonam, aztreonam macrolide, clarithromycin, dirithromycin, roxithromycin, telithromycin, azithromycin, bismuth subsalicylate, vancomycin, streptomycin, fidaxomicin, amikacin, arbekacin, neomycin, netilmicin, paromomycin, rhodostreptomycin, tobramycin, apramycin, and a combination thereof.

Embodiment 75. The method of any one of preceding claims, wherein said subject is pretreated with an anti-inflammatory drug prior to administration of said composition.

Embodiment 76. The method of any one of preceding claims, wherein said composition comprises non-pathogenic spores of one or more, two or more, three or more, or four or more *Clostridium* species selected from the group consisting of *Clostridium absonum, Clostridium argentinense, Clostridium baratii, Clostridium botulinum, Clostridium cadaveris, Clostridium carnis, Clostridium celatum, Clostridium chauvoei, Clostridium clostridioforme, Clostridium cochlearium, Clostridium fallax, Clostridium felsineum, Clostridium ghonii, Clostridium glycolicum, Clostridium haemolyticum, Clostridium hastiforme, Clostridium histolyticum, Clostridium indolis, Clostridium irregulare, Clostridium limosum, Clostridium malenominatum, Clostridium novyi, Clostridium oroticum, Clostridium paraputrificum, Clostridium perfringens, Clostridium piliforme, Clostridium putrefaciens, Clostridium putrificum, Clostridium sardiniense, Clostridium sartagoforme, Clostridium scindens, Clostridium septicum, Clostridium sordellii, Clostridium sphenoides, Clostridium spiroforme, Clostridium sporogenes, Clostridium subterminale, Clostridium symbiosum, Clostridium tertium, Clostridium tetani, Clostridium welchii,* and *Clostridium villosum.*

Embodiment 77. The method of claim 1, wherein said composition comprises purified, isolated, or cultured viable non-pathogenic *Clostridium* and a plurality of purified, isolated, or cultured viable non-pathogenic microorganisms from one or more genera selected from the group consisting of *Collinsella, Coprococcus, Dorea, Eubacterium,* and *Ruminococcus.*

Embodiment 78. The method of claim 1, wherein said composition comprises a plurality of purified, isolated, or cultured viable non-pathogenic microorganisms from one or more genera selected from the group consisting of *Clostridium, Collinsella, Coprococcus, Dorea, Eubacterium,* and *Ruminococcus.*

Embodiment 79. The method of claim 77, wherein said composition comprises two or more genera selected from the group consisting of *Collinsella, Coprococcus, Dorea, Eubacterium,* and *Ruminococcus.*

Embodiment 80. The method of claim 77, wherein said composition comprises two or more genera selected from the group consisting of *Coprococcus, Dorea, Eubacterium,* and *Ruminococcus.*

Embodiment 81. The method of claim 77 or 78, wherein said plurality of viable non-pathogenic microorganisms comprise one or more, two or more, three or more, four or more, or five or more species selected from the group consisting of *Coprococcus catus, Coprococcus comes, Dorea longicatena, Eubacterium eligens, Eubacterium hadrum, Eubacterium hallii, Eubacterium rectale,* and *Ruminococcus torques.*

Embodiment 82. The method of any one of preceding claims, wherein said method eliminates or reduces one or more recurrent diverticulitis symptoms selected from the group consisting of left lower quadrant pain, shifting bowel habits, nausea, vomiting, constipation, diarrhea, flatulence, and bloating, abscess, phlegmon, fistula, stricture, stenosis, obstruction, bleeding, and perforation.

Embodiment 83. The method of any one of preceding claims, wherein said method further comprises administering a 5-aminosalicylic acid agent, a corticosteroid, an immunosuppressant, or a combination thereof.

Embodiment 84. The method of any one of preceding claims, wherein said method further comprises administering 5-aminosalicylic acid or a derivative thereof, Sulfasalazine or a derivative thereof, or a combination thereof.

EXAMPLES

Example 1

Preparation of Fecal Microbiota

Fecal microbiota is prepared essentially according to protocols published in US2014/0147417 or WO2014/152484. Summarized below is an exemplary protocol.

Potential fecal microbiota donors are screened according to a list of criteria used to exclude unsuitable donors. Potential fecal microbiota donors are excluded if they have received antibiotics, laxatives, diet pills, immunomodulators or chemotherapy in the preceding three months. Potential fecal microbiota donors are excluded if they have a history of all known infectious diseases, morbid obesity, diabetes, irritable bowel syndrome, inflammatory bowel disease, chronic diarrhea, constipation, colorectal polyps or cancer, a compromised immune system, metabolic syndromes, chronic fatigue syndrome, major GI surgery, or other diseases or conditions potentially associated with specific changes in fecal microbiota. Potential fecal microbiota donors are excluded if they exhibit positive laboratory tests for C-reactive protein, erythrocyte sedimentation rate, hepatitis A, hepatitis B, hepatitis C, human immunodeficiency virus, or syphilis. Potential fecal microbiota donors are excluded if they exhibit a positive test for stool ova or parasites. Potential fecal microbiota donors are excluded if they engage in high-risk sexual behaviors, have been incarcerated, or received any tattoos or body piercings in areas that have had disease epidemics within the past three months.

Donor fecal material (fresh feces) is collected in a sterilized container, then it is transferred to a blender. Approximately 500-1000 mL 0.9% saline solution is added to the blender and thoroughly mixed with the fecal sample. The resulting suspension is filtered at least 4 times through strainers prior to collecting a final suspension. The final suspension is centrifuged in 50 mL tubes at 1200×g for 3 minutes. The supernatant is discarded and the pellet is gently resuspended in approximately 50 mL of sterile 0.9% saline solution. The centrifugation and resuspension steps are repeated 2 to 4 additional times. Upon the final centrifugation, the supernatant is discarded. If the fecal microbiota is to be used immediately, the resultant pellet is resuspended in 1.5-volumes of 0.9% saline solution by gently mixing. If the fecal microbiota is to be stored, the resultant pellet is resuspended in 10% sterile glycerol and stored at −80 degrees Centigrade. If fecal microbiota are frozen, they are warmed to room temperature prior to administration to a patient. If fecal microbiota is lyophilized, the lyoprotectant formulation and lyophilization procedure follow essentially those described in US 2016/0331791, published Nov. 17, 2016.

Example 2

Treatment of Recurrent Diverticulitis with FMT

A first, 67 year old patient experienced high-frequency recurrent attacks of diverticulitis. At times, his recurrent attacks occurred on almost a monthly basis which resulted in frequent emergency room visits and intravenous administration of antibiotics. The attacks recurred despite him being on antibiotic prophylaxis, mesalamine therapy, or salazopyrin treatment. The patient eventually resorted to Fecal Microbiota Transplantation (FMT). He was given a five day infusion of liquid, homogenized fresh donor stool which was initially infused through a colonoscope and later via four enema infusions. At the 3-month check-up following the infusions, the patient reported no further attacks and at the twelve-month check-up, there was no recurrent attack of diverticulitis. At the last review five years after the FMT, he was free of any recurrent diverticulitis in spite of the fact that he continued to have what appeared to be quite extensive diverticular disease previously documented by colonoscopy and CT scan.

A second, 59-year-old female patient suffered from recurrent diverticulitis. On one occasion, she had developed a peri-diverticular abscess and had a prolonged stay in hospital. She was advised to have a colectomy of the area where the diverticulitis was present. The patient refused to undergo resection of sigmoid colon with diverticulae. She slowly recovered, became virtually asymptomatic, and left the hospital. However, in a short while, she continued to have relapsing attacks of diverticulitis taking her to hospital every few months. She was ultimately referred for assessment for prophylactic treatment. Various treatments were attempted with little success, including treatment for constipation using oral vancomycin, rifaximin to suppress bloating, laxatives, and olsalazine—all of which had previously been asserted to marginally reduce recurrent diverticulitis. Finally, the patient received Fecal Microbiota Transplantation and she underwent five infusions. The first infusion was done by colonosocpe and then by rectal infusion. She experienced no further attacks for three years. After three years, however, she suffered another attack of diverticulitis.

A third, 71-year-old female patient was referred by a surgeon for FMT because of recurrent diverticulitis. This patient was not well enough to undergo resection of her left colon due to other co-morbidities. The patient underwent a five day FMT infusion treatment with the initial infusion via a colonoscope and then with enemas of fresh donor stool homogenized to a liquid format. She then underwent 'top up' infusions every week for 4 weeks. Her recurrent diverticular disease resolved for three years at the time of follow up.

Example 3

Oral Capsule Treatment Protocol (Short Regimen) for Recurrent Diverticulitis

Patients are divided into four groups (Groups 1 to 4). Group 1 patients are administered a pre-treatment of antibiotics (e.g., Vancomycin, Metronidazole, and Colchicine) until the patient shows signs of improved bowel movements. Group 2 receives no antibiotics. Both Groups 1 and 2 receive a pre-colonoscopy bowel prep followed by capsule FMT. Groups 3 and 4 receive no bowel prep while Group 3, not group 4, also receive an antibiotic pretreatment. Capsules are administered for 2 weeks as follows: two capsules (each containing $10^9$ to $10^{11}$ bacterial organisms), given twice-a-day for 4 days, two capsules twice-a-day every other day for 10 days. High dose capsules (total cell count of about $10^{12}$) are used in loading doses (also called treatment doses) for the initial 4 days. Lower dose capsules (total cell count of about $10^9$) are used in maintenance doses for the subsequent 10 days. In patients receiving antibiotic pretreatment, capsules are administered one day after ceasing antibiotics. Patient symptoms are observed and clinical examination is performed before, during and post oral capsule treatment. Pre, during and post-treatment DNA metagenomics (2-4 days; 1 week; 6 weeks; 12 weeks) are also carried out.

Example 4

Oral Capsule Treatment Protocol (Long Regimen) for Recurrent Diverticulitis

Patients are divided into four groups (Groups 1 to 4). Group 1 patients are administered a pre-treatment of antibiotics (e.g., Vancomycin, Metronidazole, and Colchicine if constipation is an issue) until the patient shows signs of improved bowel movements. Group 2 receives no antibiotics. Both Groups 1 and 2 receive a pre-colonoscopy bowel prep followed by capsule FMT. Groups 3 and 4 receive no bowel prep while Group 3, not group 4, also receive an antibiotic pretreatment. Capsules are administered for 18 weeks or more, as follows: two capsules twice-a-day for 14 days, two capsules twice-a-day every other day for 14 days, 4 capsules twice-a-week for 14 days, and 4 capsules once-a-week (e.g., each Monday) for 12 weeks. High dose capsules (total cell count of about $10^{12}$) are used in loading doses (also called treatment doses) for the initial 4 weeks. Lower dose capsules (total cell count of about $10^9$) are used in maintenance doses for the subsequent 14 weeks. In patients receiving antibiotic pretreatment, capsules are administered one day after ceasing antibiotics. Patient symptoms are observed and clinical examination is performed before, during and post oral capsule treatment. Pre, during and post-treatment DNA metagenomics (2-4 days; 1 week; 6 weeks; 12 weeks) are also carried out.

As various modifications could be made in the constructions and methods herein described and illustrated without departing from the scope of the disclosure, it is intended that all matter contained in the foregoing description shall be interpreted as illustrative rather than limiting. The breadth and scope of the present disclosure should not be limited by any of the above-described exemplary embodiments, but should be defined only in accordance with the following claims appended hereto and their equivalents. All patent and non-patent documents cited in this specification are incorporated herein by reference in their entirety.

The invention claimed is:

1. A method for treating recurrent diverticulitis in a subject in need thereof, said method comprising administering to said subject a pharmaceutically active dose of a therapeutic composition comprising a community of live non-pathogenic fecal bacteria derived from a stool of a healthy human donor, wherein said treating alleviates at least one symptom of said recurrent diverticulitis for at least 3 months.

2. The method of claim 1, wherein said recurrent diverticulitis is at a clinical stage selected from the group consisting of Stages I to IV.

3. The method of claim 1, wherein said composition comprises a non-selected fecal microbiota.

4. The method of claim 1, wherein said dose is administered at least once daily for at least 2 weeks.

5. The method of claim 1, wherein said dose is administered at least twice weekly for at least 2 weeks.

6. The method of claim 1, wherein said dose is administered at least twice weekly for at least 4 weeks.

7. The method of claim 1, wherein said dose is administered at least twice weekly for at least 8 weeks.

8. The method of claim 1, wherein said dose is administered at least three times weekly for at least 4 weeks.

9. The method of claim 1, wherein said therapeutic composition comprises both live nonpathogenic fecal bacteria and a non-cellular fecal filtrate.

10. The method of claim 1, wherein said method comprises a first dosing schedule followed by a second dosing schedule, wherein said second dosing schedule comprises a maintenance dose lower or equal to the dose of said first dosing schedule.

11. The method of claim 1, wherein said composition is formulated as a delayed or gradual enteric release form.

12. The method of claim 1, wherein said composition is formulated as an enteric coated capsule or an acid-resistant capsule.

13. The method of claim 1, wherein said pharmaceutically active dose is from $10^8$ to $10^{14}$ cfu or total number of cells.

14. The method of claim 3, wherein said fecal microbiota comprises a donor's entire fecal microbiota.

15. The method of claim 1, wherein said composition is in a liquid, frozen, freeze-dried, spray-dried, lyophilized, or powder form.

16. The method of claim 1, wherein said composition comprises a cryoprotectant selected from the group consisting of polyethylene glycol, skim milk, erythritol, arabitol, sorbitol, glucose, fructose, alanine, glycine, proline, sucrose, lactose, ribose, trehalose, dimethyl sulfoxide (DMSO), glycerol, or a combination thereof.

17. The method of claim 1, wherein said composition is substantially free of non-living matter.

18. The method of claim 1, wherein said subject is pretreated with an antibiotic prior to administration of said composition.

19. The method of claim 1, wherein said at least one symptom of said recurrent diverticulitis is selected from the group consisting of left lower quadrant pain, shifting bowel habits, nausea, vomiting, constipation, diarrhea, flatulence, and bloating, abscess, phlegmon, fistula, stricture, stenosis, obstruction, bleeding, and perforation.

20. The method of claim 1, wherein said method further comprises administering a 5-aminosalicylic acid agent, a corticosteroid, an immunosuppressant, or a combination thereof.

* * * * *